(12) United States Patent
Lorenzo

(10) Patent No.: US 10,751,066 B2
(45) Date of Patent: *Aug. 25, 2020

(54) ANEURYSM DEVICE AND DELIVERY SYSTEM

(71) Applicant: DePuy Synthes Products, Inc., Raynham, MA (US)

(72) Inventor: Juan Lorenzo, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 302 days.

This patent is subject to a terminal disclaimer.

(21) Appl. No.: 15/903,860

(22) Filed: Feb. 23, 2018

(65) Prior Publication Data

US 2018/0242979 A1    Aug. 30, 2018

Related U.S. Application Data

(60) Provisional application No. 62/462,685, filed on Feb. 23, 2017.

(51) Int. Cl.
*A61B 17/12* (2006.01)
*A61B 90/00* (2016.01)
*A61B 17/00* (2006.01)

(52) U.S. Cl.
CPC .. *A61B 17/12172* (2013.01); *A61B 17/12031* (2013.01); *A61B 17/12113* (2013.01); *A61B 17/1214* (2013.01); *A61B 2017/00867* (2013.01); *A61B 2017/1205* (2013.01); *A61B 2017/12054* (2013.01); *A61B 2017/12068* (2013.01); *A61B 2090/3966* (2016.02)

(58) Field of Classification Search
CPC ........ A61B 17/12022; A61B 17/12031; A61B 17/12109; A61B 17/12113; A61B 17/12118; A61B 17/1214; A61B 17/12168; A61B 17/12172; A61B 2017/1205; A61B 2017/12054
See application file for complete search history.

(56) References Cited

U.S. PATENT DOCUMENTS 5,334,210 A * 8/1994 Gianturco ........ A61B 17/12022
604/907
6,331,184 B1 * 12/2001 Abrams ........... A61B 17/12022
604/164.09

(Continued)

FOREIGN PATENT DOCUMENTS

| WO | 2005117718 A1 | 12/2005 |
|---|---|---|
| WO | 2015171268 A2 | 11/2015 |
| WO | 2015160721 A1 | 10/2018 |

OTHER PUBLICATIONS

International Search Report dated May 25, 2018 during the prosecution of PCT/US2018/019330.

*Primary Examiner* — Ryan J. Severson
(74) *Attorney, Agent, or Firm* — Troutman Pepper Hamilton Sanders LLP

(57) ABSTRACT

The present disclosure relates to a self-expanding braided tubular member for treating an aneurysm. The braid can include a distal implant end opposite a proximal implant end. Translating the braid distally from within a tubular delivery member can cause the distal implant end to invert and fold into itself thereby forming an occlusive sack for occluding an aneurysm.

14 Claims, 19 Drawing Sheets

(56) References Cited

U.S. PATENT DOCUMENTS

| | | | |
|---|---|---|---|
| 6,346,117 B1 * | 2/2002 | Greenhalgh | A61B 17/12022 606/200 |
| 6,391,037 B1 | 5/2002 | Greenhalgh | |
| 6,506,204 B2 | 1/2003 | Mazzocchi et al. | |
| 6,846,316 B2 * | 1/2005 | Abrams | A61B 17/12022 604/164.09 |
| 7,410,482 B2 * | 8/2008 | Murphy | A61B 17/12022 606/1 |
| 8,021,416 B2 * | 9/2011 | Abrams | A61B 17/12022 623/1.23 |
| 8,025,668 B2 * | 9/2011 | McCartney | A61B 17/221 606/106 |
| 8,777,974 B2 | 7/2014 | Amplatz et al. | |
| 8,974,512 B2 | 3/2015 | Aboytes et al. | |
| 8,998,947 B2 | 4/2015 | Aboytes et al. | |
| 9,055,948 B2 | 6/2015 | Jaeger et al. | |
| 9,232,992 B2 | 1/2016 | Heidner et al. | |
| 9,314,326 B2 | 4/2016 | Wallace et al. | |
| 9,351,715 B2 * | 5/2016 | Mach | A61B 17/0057 |
| 9,414,842 B2 * | 8/2016 | Glimsdale | A61B 17/12172 |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign | |
| 9,681,861 B2 * | 6/2017 | Heisel | A61B 17/0057 |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman | |
| 9,770,577 B2 | 9/2017 | Li | |
| 9,775,621 B2 | 10/2017 | Tompkins et al. | |
| 9,775,706 B2 | 10/2017 | Paterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman | |
| 9,833,252 B2 | 12/2017 | Sepetka | |
| 9,833,604 B2 | 12/2017 | Lam | |
| 9,833,625 B2 | 12/2017 | Waldhauser et al. | |
| 9,955,976 B2 * | 5/2018 | Hewitt | A61B 17/12031 |
| 10,307,148 B2 * | 6/2019 | Heisel | A61B 17/0057 |
| 10,327,781 B2 * | 6/2019 | Divino | A61B 17/1219 |
| 10,342,546 B2 * | 7/2019 | Sepetka | A61B 17/12031 |
| 2003/0171739 A1 | 9/2003 | Murphy et al. | |
| 2003/0195553 A1 * | 10/2003 | Wallace | A61B 17/12022 606/200 |
| 2005/0251200 A1 | 11/2005 | Porter | |
| 2006/0052816 A1 | 3/2006 | Bates et al. | |
| 2006/0064151 A1 | 3/2006 | Guterman | |
| 2006/0247572 A1 * | 11/2006 | McCartney | A61B 17/221 604/19 |
| 2007/0106311 A1 * | 5/2007 | Wallace | A61F 2/06 606/151 |
| 2007/0186933 A1 * | 8/2007 | Domingo | A61B 17/12022 128/207.15 |
| 2007/0265656 A1 * | 11/2007 | Amplatz | A61B 17/0057 606/200 |
| 2008/0281350 A1 | 11/2008 | Sepetka | |
| 2009/0099647 A1 * | 4/2009 | Glimsdale | A61B 17/12172 623/1.35 |
| 2010/0023046 A1 | 1/2010 | Heidner | |
| 2010/0069948 A1 * | 3/2010 | Veznedaroglu | A61B 17/12022 606/194 |
| 2010/0324649 A1 | 12/2010 | Mattsson et al. | |
| 2011/0152993 A1 | 6/2011 | Marchand et al. | |
| 2012/0283768 A1 | 11/2012 | Cox et al. | |
| 2013/0204351 A1 | 8/2013 | Cox et al. | |
| 2014/0135812 A1 | 5/2014 | Divino et al. | |
| 2014/0200607 A1 | 7/2014 | Sepetka et al. | |
| 2015/0209050 A1 | 7/2015 | Aboytes et al. | |
| 2015/0272589 A1 | 10/2015 | Lorenzo | |
| 2015/0342613 A1 | 12/2015 | Aboytes et al. | |
| 2015/0374483 A1 | 12/2015 | Janardhan et al. | |
| 2016/0022445 A1 | 1/2016 | Ruvalcaba et al. | |
| 2016/0249934 A1 | 9/2016 | Hewitt et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu | |
| 2017/0027640 A1 | 2/2017 | Kunis et al. | |
| 2017/0027692 A1 | 2/2017 | Bonhoeffer | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero | |
| 2017/0079680 A1 | 3/2017 | Bowman | |
| 2017/0079766 A1 | 3/2017 | Wang | |
| 2017/0079767 A1 | 3/2017 | Leon-Yip | |
| 2017/0079812 A1 | 3/2017 | Lam et al. | |
| 2017/0079817 A1 | 3/2017 | Sepetka | |
| 2017/0079819 A1 | 3/2017 | Pung et al. | |
| 2017/0079820 A1 | 3/2017 | Lam et al. | |
| 2017/0086851 A1 | 3/2017 | Wallace | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein | |
| 2017/0165454 A1 | 6/2017 | Tuohy | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |

(56) References Cited

U.S. PATENT DOCUMENTS

| | | |
|---|---|---|
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0242979 A1 | 8/2018 | Lorenzo |
| 2019/0008522 A1* | 1/2019 | Lorenzo ............ A61B 17/12172 |
| 2019/0192167 A1* | 6/2019 | Lorenzo ............ A61B 17/12031 |
| 2019/0192168 A1* | 6/2019 | Lorenzo ............ A61B 17/12172 |
| 2019/0223878 A1* | 7/2019 | Lorenzo ............ A61B 17/12172 |

* cited by examiner

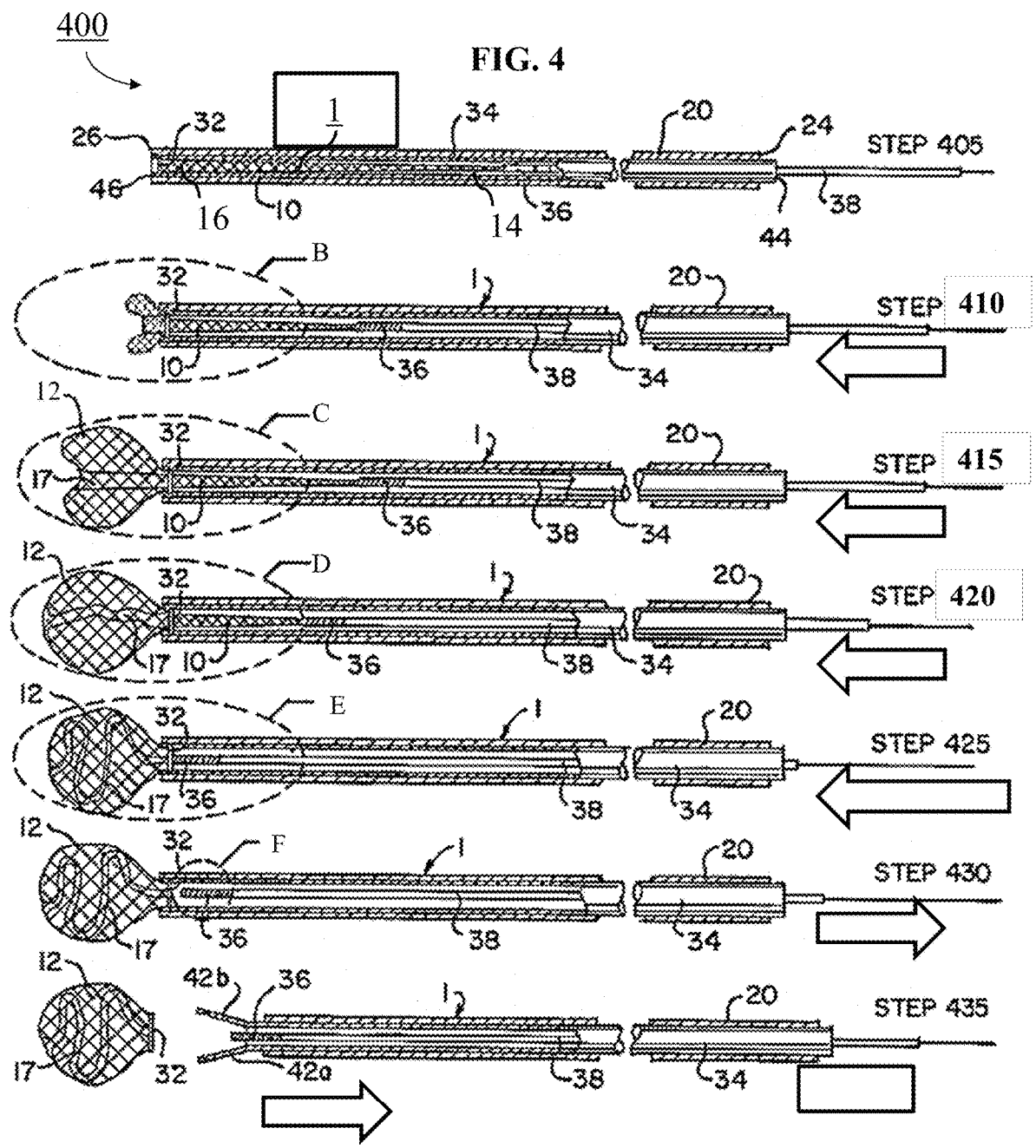

905 — a self-expanding braid inverts as it distally translates from a delivery catheter into the aneurysm 910 — the braid forms an occlusive sack that conforms to the size and/or shape of the aneurysm 915 — the braid continues distally translating and when the braid reaches the top of the aneurysm, portions of the braid cease inverting and are in a non-inverted condition 920 — the portions of the braid in the non-inverted condition distally translate and fill the occlusive sack inside the aneurysm to a predetermined packing density

1005 — selectively positioning a microcatheter in the vasculature

1010 — slidably positioning a delivery system of the occlusion device within the microcatheter, the delivery system comprising a delivery tube comprising a distal end and a proximal end and a pushing mechanism slideably disposed within the delivery tube, the pushing mechanism comprising a distal end and a proximal end 1015 — slidably positioning a self-expanding braid of the occlusion device within the delivery tube, the braid comprising a distal end and a proximal end 1020 — detachably attaching the proximal end of the braid to the distal end of the pushing mechanism 1025 — advancing the delivery system to the vasculature to the aneurysm 1030 — distally sliding the braid, by the pushing mechanism, in the delivery tube toward the aneurysm thereby causing the braid to invert and/or radially expand whiling moving from a collapsed condition within the delivery tube to a deployed condition within the aneurysm as the distal end of the braid is moved outside and away from the distal end of the delivery tube 1035 — releasing the occlusion device and withdrawing the delivery system and the catheter from the patient

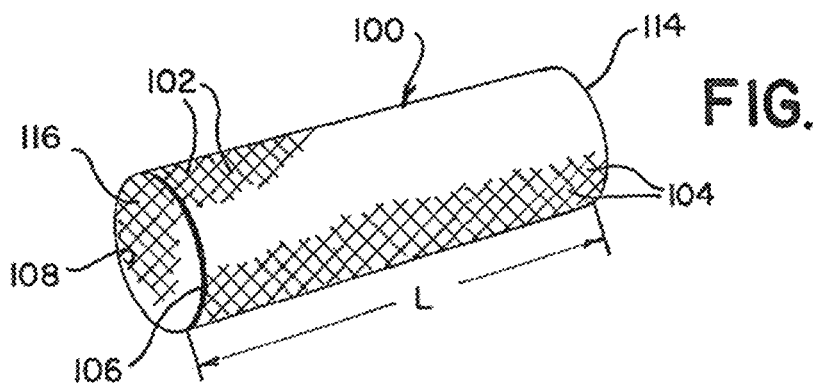
FIG. 11A
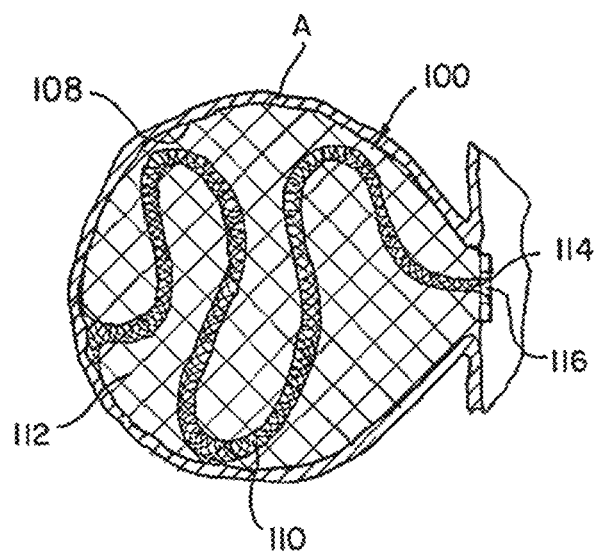
FIG. 11B
FIG. 11C
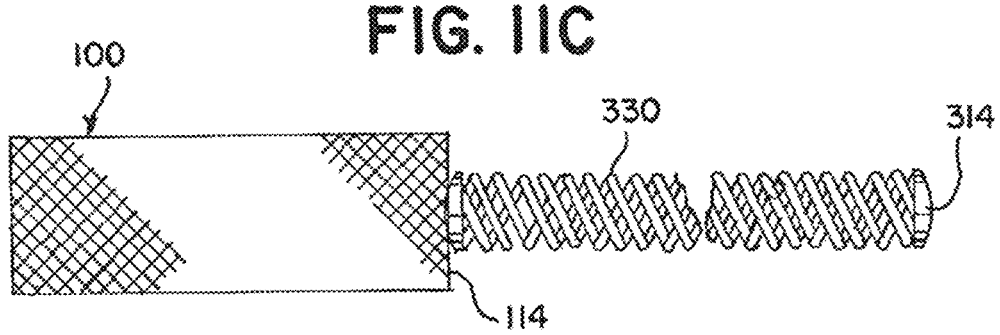

ANEURYSM DEVICE AND DELIVERY SYSTEM

CROSS REFERENCE TO RELATED APPLICATIONS

This application claims priority to U.S. provisional patent application No. 62/462,685 entitled "ANEURYSM DEVICE AND DELIVERY SYSTEM" and filed Feb. 23, 2017, the contents which are incorporated herein by reference as if set forth verbatim.

FIELD

This disclosure relates to medical instruments, and more particularly, delivery systems for a device for aneurysm therapy.

BACKGROUND

Aneurysms can be complicated and difficult to treat. For example, treatment access may be limited or unavailable when an aneurysm is located proximate critical tissues. Such factors are of particular concern with cranial aneurysms due to the presence of brain tissue surrounding cranial vessels.

Prior solutions have included endovascular treatment access whereby an internal volume of the aneurysm sac is removed or excluded from arterial blood pressure and flow.

Alternative to endovascular or other surgical approaches can include occlusion devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. One particular type of occlusive approach endeavors to deliver and treat the entrance or "neck" of the aneurysm as opposed to the volume of the aneurysm. In such "neck" approaches, by minimizing blood flow across the neck, then a venostasis in the aneurysm may be achieved. In turn, a thrombotic mass may naturally form without having to deliver embolic materials, as previously described. This is preferable to masses formed from embolic material since a natural mass can improve healing by reducing possible distention from arterial walls and permits reintegration into the original parent vessel shape along the neck plane of the aneurysm. It is understood that the neck plane is an imaginary surface where the inner most layer of the parent wall would be but for the aneurysm. However, neck-occlusive approaches are not without drawbacks. It is typical for neck-occlusive approaches to fail to impede flow into blood vessels while also blocking the aneurysm neck in the parent vessel. This can unintentionally lead to severe damage if the openings of the vessels are blocked. Furthermore, embolic coils do not always effectively treat aneurysms as re-canalization of the aneurysm and/or coil compaction can occur over time.

Several embodiments of an occlusion device are described in U.S. Pat. No. 8,998,947. However, this approach relies upon the use of embolic coils or mimics the coil approach to obtain a safe packing density and therefore unnecessarily risks rupture of the aneurysm. Furthermore, this approach fails to teach a delivery system whereby an occlusion device can be re-positioned after initial positioning of its aneurysm occlusion structure to ensure patient safety associated with precise positioning.

It is therefore desirable to have a device which easily, accurately, and safely occludes a neck of an aneurysm or other arterio-venous malformation in a parent vessel without blocking flow into perforator vessels communicating with the parent vessel.

SUMMARY

In some aspects, the present disclosure relates to a medical device for treating an aneurysm. The device can include a self-expanding braided tubular implant (hereinafter "braid") with a lumen that has a distal implant end and a proximal implant end. The distal implant end can be opposite the proximal implant end. Distal translation of the braid from within a tubular delivery member can cause the distal implant end to invert and fold into itself thereby forming an occlusive sack for occluding an aneurysm.

In certain embodiments, the tubular delivery member can be disposed about the implant and have a distal end that is releasably connected to the distal implant end of the braid. The braid can have a longitudinal axis between the distal implant end and the proximal implant end. The braid can be invertible about the longitudinal axis by distally translating the braid about the axis.

In certain embodiments, the lumen of the braid can include a pre-fabricated break that is disposed between the distal and implant ends. The break can be formed from localized heat treatment zone that is kink-preventative and configured to induce gradual folding and/or inversion of the braid. The break can be disposed between the distal and implant ends. The break can be configured for the occlusive sack to form when the distal implant end is translated toward or contacts a dome of the aneurysm. In some embodiments, one or more regions or areas of the distal end of the distal implant end are substantially atraumatic or rounded and configured to minimize kinking of the braid during inversion. In certain embodiments, continuing to translate the braid upon formation of the occlusive sack can lead to formation of a second sack within the occlusive sack. Additional sacks can be formed within the first and second sacks as needed or required (e.g. to achieve a desired packing density or to further support the first and second sacks). It is understood that each sack can be formed from a respective portion of the braid inverting and folding into itself.

In certain embodiments, the proximal implant end is operable to mechanically attach to a delivery system. The delivery system can include a catheter and a pushing mechanism disposed in the catheter and/or including a hypotube, the pushing mechanism operable to translate the braid toward the aneurysm. In certain embodiments, the occlusive sack can be substantially spherical, ellipsoidal, or otherwise conformable to an asymmetric aneurysm, for example, an aneurysm with multiple sacs, irregular dome or walls. The proximal implant end can also be less pliable and/or can have less material strength than the distal implant end. An outer surface of the braid can also include a plurality of interstices (e.g. a mesh surface).

The invertibility, pliability, and/or porosity of the braid can be selectively designed for treatment of an aneurysm having a particular shape, by varying properties of the interstices among different portions of the braid.

In other embodiments, a method of delivering an occlusion device to an aneurysm in a blood vessel in a patient is disclosed. The method can include positioning an occlusion device within a delivery tube (e.g. a tube that can be pushed or caused to translate the occlusion device), the occlusion device comprising any self-expanding braid of this disclosure; distally sliding the braid towards the aneurysm from within the delivery tube; expanding a distal implant end of the braid from a collapsed condition to a deployed condition; and inverting the distal implant end of the braid to form a sack for occluding the aneurysm.

In certain embodiments, the distal implant end of the braid begins expanding immediately as the braid exits a distal end of the delivery tube. In certain embodiments, when the sack is formed, it can include a predetermined packing density or density range. In certain embodiments, the method can include positioning a microcatheter within the vasculature and then positioning the occlusion device assembled with the delivery tube inside the microcatheter; and delivering the occlusion device and the delivery tube assembled with the microcatheter to the aneurysm. In certain embodiments, the method can also include: imaging the sack with respect to the aneurysm; determining whether the aneurysm is occluded by the sack; and distally or proximally sliding the braid to adjust the sack and to occlude the aneurysm.

In certain embodiments, imaging the sack with respect to the aneurysm includes determining whether a necessary packing setting for the sack to occlude the aneurysm and moving the braid (e.g. by distally or proximally sliding the braid) to adjust the sack.

In other embodiments, a method of delivering an occlusion device to an aneurysm in a blood vessel in a patient is disclosed. The method can include: positioning the occlusion device within a delivery tube, the occlusion device comprising a self-expanding braid; distally sliding a braid toward the aneurysm; expanding (e.g. radially expanding) a distal implant end of the braid from a collapsed condition to a deployed condition as the braid approaches a dome of the aneurysm; and inverting the distal implant end of the braid to form an occlusive sack that packs the aneurysm to a predetermined packing density and occludes the aneurysm.

In certain embodiments, the braid includes a first break that is defined by a size of the sack for occluding the aneurysm. The braid can also include a second break proximal of the first break. In this respect, the method can also include distally sliding the braid toward the aneurysm after formation of the first sack; and inverting the braid at the second break to form a second sack internal to the first sack.

In certain embodiments, the method can also include: distally sliding the braid toward the aneurysm after formation of the first sack; and inverting the braid to form a second sack internal to the first sack.

In certain embodiments, the method can also include: continuing to distally slide the braid toward the aneurysm after formation of the first sack thereby packing the sack with one or more unexpanded portions of the braid.

In certain embodiments, the method can also include: determining a position of the sack relative to the aneurysm and if the position fails to fit or conform to the sack, then the braid may be proximally translated thereby causing the sack to collapse back into the braid; and withdrawing the braid from the aneurysm.

In other embodiments, this disclosure relates to a delivery system for an occlusive device for treating an aneurysm. In some embodiments, the delivery system can include a delivery tube that includes a distal end and a proximal end. The delivery tube can be slidably disposed within a microcatheter. A pushing mechanism can be slidably disposed within the delivery tube. The occlusive device can be slidably disposed within the delivery tube and mechanically attached to the pushing mechanism. The occlusive device can include a braid having a lumen with a distal implant end opposite a proximal implant end. The pushing mechanism can be operable to distally translate the occlusive device to a deployed condition within the aneurysm, wherein distally translating the braid to the deployed condition causes the distal implant end to invert and fold into itself thereby forming an occlusive sack for the aneurysm.

In certain embodiments, the proximal implant end of the braid may be capable of mechanical attachment, detachable or otherwise, to the distal end of the pushing mechanism.

In other embodiments, at least a portion of the braid defines a plurality of interstices with openings for occlusion of the aneurysm. In other embodiments, the proximal implant end of the braid can be attached to and foldable over an inner portion of the pushing mechanism.

In other embodiments, the braid can be attached to and foldable over an inner portion of the pushing mechanism. The braid may also be fillable as the braid is folded. In certain embodiments, the braid can be invertible as the braid distally slides and exits the delivery tube. The sack may be a collapsible cage-like vaso-occlusive structure.

In other embodiments, the distal end of the delivery member can include opposed gripping arms (e.g., upper and lower). One or both gripping arms can be pivotable toward the other gripping arm to release the braid from the delivery tube when the braid forms a sack about the. In other embodiments, the pushing mechanism can also include an inner passage through which at least one embolic coil is insertable into the braid when the braid forms a sack within the aneurysm.

In other embodiments, the pushing mechanism can include radiopaque material (e.g. the distal end, the proximal end, etc.).

In other embodiments, a method is disclosed for delivering an occlusion device to an aneurysm in a blood vessel in a patient. The method includes: positioning a delivery system of the occlusion device within a microcatheter in the vasculature, the delivery system including a delivery tube having a distal end and a proximal end. The delivery system may also include a pushing mechanism that is slidably disposed within the delivery tube, the pushing mechanism comprising a distal end and a proximal end. The method may include slidably positioning a self-expanding braid of the occlusion device within the delivery tube, the braid comprising a distal end and a proximal end; detachably attaching the proximal end of the braid to the distal end of the pushing mechanism; selectively inserting the microcatheter with the delivery system and the occlusion device into vasculature of the patient to reach the aneurysm; distally sliding the braid, by the pushing mechanism, in the delivery tube toward the aneurysm thereby causing the braid to radially expand and move from a collapsed condition within the delivery tube to a deployed condition within the aneurysm as the distal end of the braid is moved outside and away from the distal end of the delivery tube; and releasing the occlusion device and withdrawing the microcatheter and the delivery system from the patient.

In other embodiments, the method can also include: forming, by the braid, a sack within the aneurysm by distally sliding the braid to the deployed condition; distally sliding the pushing mechanism to the distal end of delivery tube until the braid folds; and folding the braid thereby filling the sack and securing the occlusion device within the aneurysm to occlude flow into the aneurysm.

In other embodiments, the method can also include: forming the sack within the aneurysm by inverting the braid as the braid distally slides and exits the delivery tube and/or bulges against a wall of the aneurysm.

In other embodiments, the method can also include: deflecting the pushing mechanism as the braid is inverted and reaches a dome of the aneurysm; filling the sack as the braid is inverted; and/or continuing to distally translate, by the pushing mechanism, the braid into the aneurysm until the proximal end of the braid reaches the distal end tip of the pushing mechanism.

In other embodiments, the method can also include: attaching the proximal end of the braid to an inner portion of the pushing mechanism; and/or filling the sack by folding the braid until the braid is at least level with a neck of the aneurysm.

In other embodiments, the method can also include: forming, by the braid, a sack within the aneurysm by distally sliding the braid to the deployed condition; forming a gripping mechanism for detaching the sack from the delivery system, the gripping mechanism being formed by a pair of opposed gripping arms formed at a distal end of the delivery tube, one or both gripping arms being pivotable toward the other gripping arm; and/or detaching, by the grabbing mechanism of the delivery system, the sack from the delivery system by pivoting one or both arms away from the other.

In other embodiments, the method can also include: inserting at least one embolic coil through an inner passage of the pushing mechanism and into the sack to adjust the packing density.

In other embodiments, the method can include forming, by inverting the braid, a first occlusive sack within the aneurysm by distally sliding the braid from the delivery tube toward the aneurysm; distally sliding the braid toward the aneurysm after formation of the first sack; and inverting the braid to form a second sack within the first sack. Forming the first and/or second sack can cause flow into the aneurysm to be deflected, diverted, and/or slowed.

In other embodiments, the method can include forming, by inverting the braid, a first occlusive sack within the aneurysm by distally sliding the braid from the delivery tube toward the aneurysm; distally sliding the braid toward the aneurysm after formation of the first sack; inverting the braid to form a second sack within the first sack; distally sliding the braid toward the aneurysm after formation of the second sack; and inverting the braid to form a third sack within the first and second sacks. Forming the first, second and/or third sack can cause flow into the aneurysm to be deflected, diverted, and/or slowed. It is contemplated that only one sack could be used or more than three sacks could be formed and used for purposes of deflecting, diverting, and/or slowing flow into the aneurysm.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 4 is a flow diagram for a method of delivering an occlusion device to the vasculature using the herein disclosed delivery system;

FIG. 9 is a flow diagram for a method of delivering an occlusion device.

FIG. 10 is a flow diagram for a method of delivering an occlusion device using the herein disclosed delivery system.

FIG. 11A depicts an example braid of this disclosure.

FIG. 11B depicts an example braid of this disclosure deployed.

FIG. 11C depicts an example braid with embolic coil of this disclosure.

DETAILED DESCRIPTION

Figure 1:
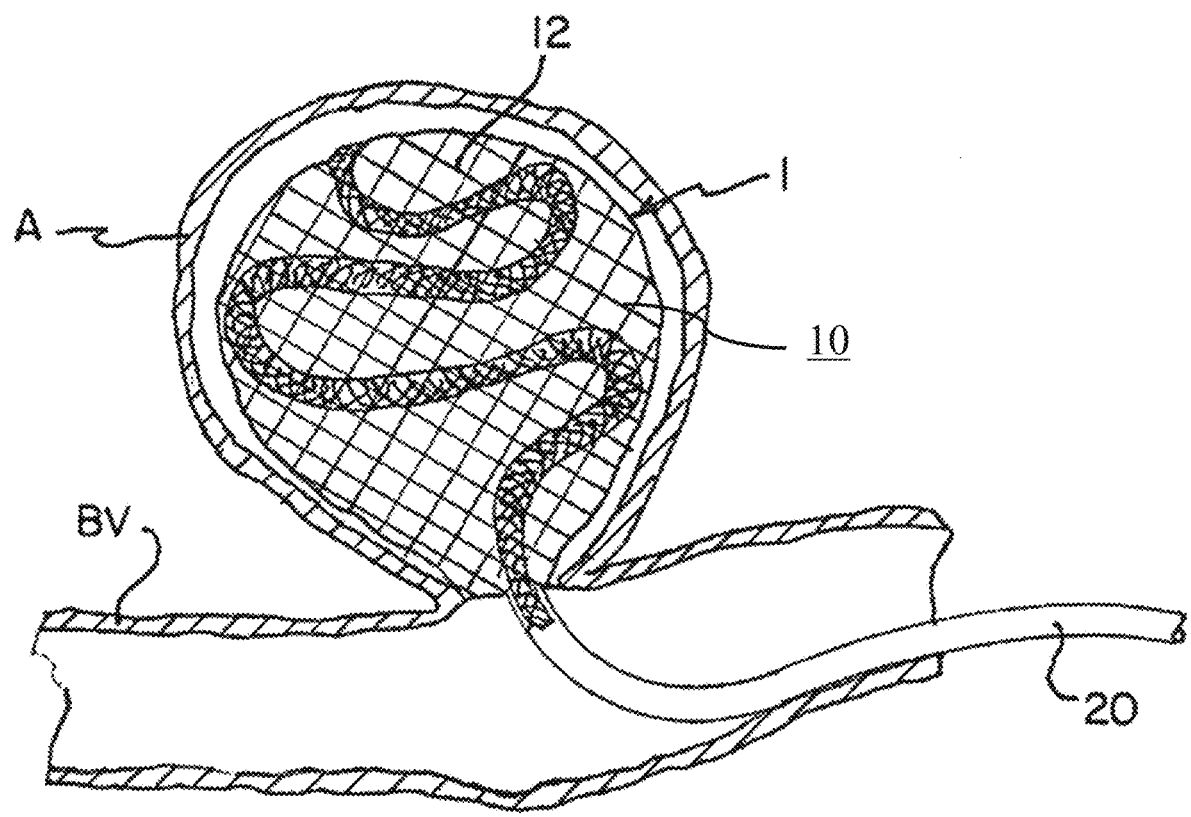
FIG. 1 depicts an example occlusion device of this disclosure deployed into an aneurysm.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braid body to the vasculature of a subject.

Cerebrovascular aneurysms are known to be treated using embolic coils, which are delivered to the aneurysm sack via a microcatheter and detached in situ. It is understood that "packing density" is the volume of the aneurysm sack occupied by the coil mass. In previous coil approaches, multiple coils (e.g. five coils) have been used to pack the aneurysms and the packing density can typically range between 15-25%, depending on the aneurysm size. The herein disclosed device improves on use of embolic coils by using a single device without a need for even a single coil to pack the device. Instead, the disclosed device is operable to seal the aneurysm neck and pack the aneurysm to a higher packing density than using coils. In practice, the packing density can be as increased 25-50% depending on the length of braid in the aneurysm, or double what can be achieved with conventional coils. However, the multiple braid layers formed as the braid packs the aneurysm may mean that a lower packing density may achieve blood flow alteration and coagulation in a way that a lower packing density may achieve the same level of occlusion. This allows for the aneurysm neck to heal.

In contrast, in previous embolic-based approaches, packing the aneurysm required in placement of coils into the aneurysm sack until the aneurysm obtained the desired packing density to occlude the aneurysm. However, obtaining such a packing density was difficult, time consuming, and aneurysm morphology (e.g. wide neck, bifurcation, etc.), and the like required ancillary devices such a stents or balloons to support the coil mass and obtain the desired packing density. Furthermore, aneurysms treated with multiple coils often reanalyze or compact as a result of poor coiling, lack of coverage across the aneurysm neck, as a result of flow, or even aneurysm size.

The occlusion device 1 and corresponding delivery system 30 disclosed herein addresses the drawbacks of previous approaches, including low packing density, compaction and recanalization of aneurysms.

Turning to FIG. 1, an example occlusion device 1 of this disclosure is shown deployed into an aneurysm A of blood vessel BV but not yet released from its delivery system. The catheter 20 has been delivered to the aneurysm A and as shown and discussed more particularly below, occlusive sack 12 of braided tubular implant 10 (hereinafter also referred to "braid" or "braid 10") of device 1 has formed a predetermined shape and structure that outlines and supports the walls of the aneurysm A so as to occlude aneurysm A.

Figure 2:
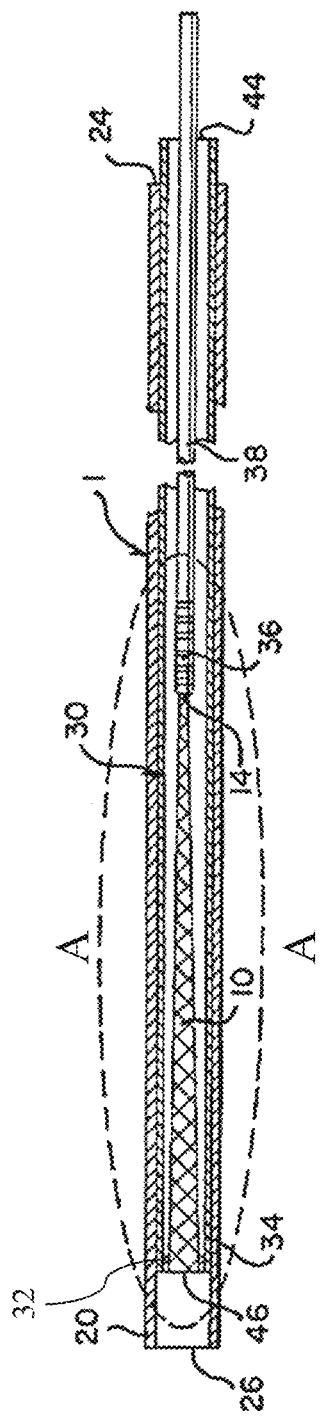
FIG. 2 is a schematic side view of an exemplary delivery system with an occlusion device held in a collapsed condition within a microcatheter.
Figure 3:
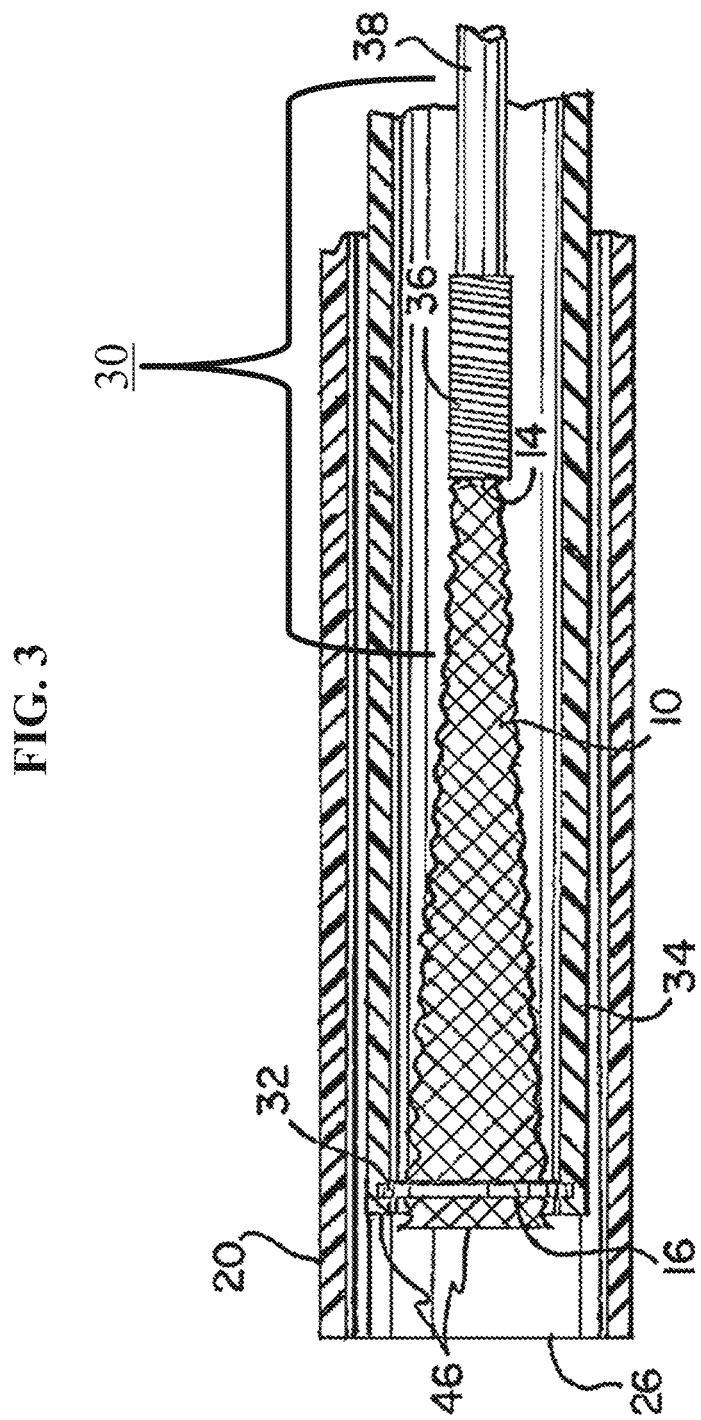
FIG. 3 is an enlarged schematic side view of the delivery system of FIG. 2 along section A-A.

FIG. 2 depicts a schematic side view of braid 10 and delivery system 30 prior to being positioned in a location of interest in the vasculature for occluding aneurysm A. The braid 10 can include a lumen with a distal implant end 16 opposite a proximal implant end 14, as shown more particularly in FIG. 3. Specifically, FIG. 3 is an enlarged schematic side view of the delivery system of FIG. 2 along section A-A prior to deployment. System 30 can include a pusher delivery tube 34 with an inner lumen and a braid pushing mechanism 38. System 30 can deliver an occlusive device, which includes braid 10, to a location of interest (e.g. a lesion site) using a microcatheter 20. System 30 may be preplaced in microcatheter 20. In certain embodiments, microcatheter 20 can be pre-placed, with or without system 30, at a level of the aneurysm neck and used to track the device 1 to the lesion. Mechanism 38 may be tubular, solid, elongate, and/or be pliable to be able to pass through tortuous pathways of the vasculature within delivery tube 34 and/or microcatheter 20. Mechanism 38 can include an inner lumen and be disposable or capable of functioning with a hypotube. For example, a hypotube can be attached or in communication with mechanism 38 to distally slide mechanism 38 toward the aneurysm A.

In this respect, mechanism 38 may be slidably disposed within delivery tube 34, wherein mechanism 38 can be in mechanical connection with braid 10 at attachment 36. When braid 10 is mechanically attached to pushing mechanism 38 at attachment 36, distally translating, sliding, or otherwise moving mechanism 38 toward the aneurysm can cause a distal implant end 16 of braid 10 to begin moving from a collapsed condition to a deployed condition, as discussed below. Both delivery tube 34 and mechanism 38 can extend from the proximal 24 to the distal end 26 of microcatheter 20.

It is understood that braid 10 can include a self-expanding braid for treating an aneurysm. The inner lumen of braid 10 can form a self-expanding multi-filament outer surface that can include a mesh. It can be seen that mechanism 38 is disposed proximal of braid 10 and braid 10 is in communication with mechanism 38 across attachment 36 at proximal implant end 14. Braid 10 may be attached to attachment 36 by being crimped thereon or by a detachable connection. In certain embodiments, proximal implant end 14 may be inserted within the distal end of mechanism 38 at attachment 36 wherein mechanism 38 can then be attached therewith or thereon. However, attachment 36 is not so limited and instead braid 10 may be slidably, detachably inserted over or otherwise with attachment 36.

Prior to deployment within an aneurysm A, distal implant end 16 of braid 10 is adjacent or in contact with distal end 46 of delivery tube 34. Delivery tube 34 may also include one or more fasteners 32 operable to securely fasten braid 10 in place prior to deployment. The area of braid 10 of distal implant end 16 adjacent or in communication with fastener 32 may be substantially atraumatic and/or rounded so to minimize kinking or other damage to the adjacent area of braid 10. Fastener 32 may include a crimping, soldering, bracing, adhesive, pressure cuff, welding, or other fastener means, including clamps, or the like, so that delivery tube 34 is secured therewith but translation of mechanism 38 and braid 10 is still permitted when actuation is desired.

Braid 10 may be operable to expand over the neck of the aneurysm A during delivery which can substantially reduce and/or prevent further blood flow from the parent vessel into the aneurysm sac. Portions of braid 10 on or proximate end 16 may be more pliable than portions of braid 10 on or proximate end 14 in order to induce self-expansion during delivery and inversion as braid 10 forms its predetermined, sack-like shape within aneurysm A (see, e.g., FIG. 1). The braid 10, including its outer surface, can be self-expanding and made from nitinol with interwoven platinum filaments for radiopacity. Braid 10 is not so limited, however, and any material or combination of materials can be used to form an outer surface of braid 10 can be used as needed or required.

Turning to FIG. 4, a flow diagram for a method 400 is shown for safely and precisely delivering an example braid 10 to the vasculature. As can be seen, in step 405 of method 400, the occlusion device 1 is assembled with a microcatheter 20. The assembly between microcatheter 20 and device 1 can take place before being introduced into the vasculature. In step 410, device 1, including system 30, may now have been selectively positioned at the lesion site and mechanism 38 can begin its distal translation of the braid 10. As can be seen in step 410, braid 10 begins expanding and/or inverting as its distal implant end 16 moves away from distal end 26 of catheter 20 and/or delivery end 46 (not identified in this figure) of delivery tube 34 to form sack 12 within aneurysm A being treated (see, e.g., formed sack 12 of device 1 that occludes aneurysm A of FIG. 1).

In certain embodiments, sack 12 begins being formed as braid 10 is advanced to the vicinity of the neck or dome of the aneurysm such that mechanism 38, attachment 36, and/or portions of delivery tube 34 are at the level of the neck as seen under fluoroscopy. However, device 1 is not so limited and instead braid 10 can begin inverting and folding into itself to form sack 12 as distal implant end 16 simply distally slides away from delivery tube 34 and/or catheter 20. As shown in step 415, sack 12 is now taking a generally spherical shape as braid 10 is translated distally deeper into aneurysm A and/or further away from catheter 20 and tube 34. In moving between steps 405 to 415, the outer diameter of the braid 10 radially expands to a diameter greater than the microcatheter 20 as sack 12 is formed. The braid wire count of interstices of braid 10 that may form the outer surface can vary depending of the diameter of the sack 12 or sacks needed to occlude the aneurysm. For example, in order to induce formation of the predetermined shape and strength of sack 12, distal implant end 16 of braid 10 may be more pliable than proximal implant end 14 and portions of braid 10 may vary from most pliable on or about end 16 and less pliable on or about end 14. Interstices of braid 10 may also form openings for occlusion of the aneurysm.

Figure 5A:
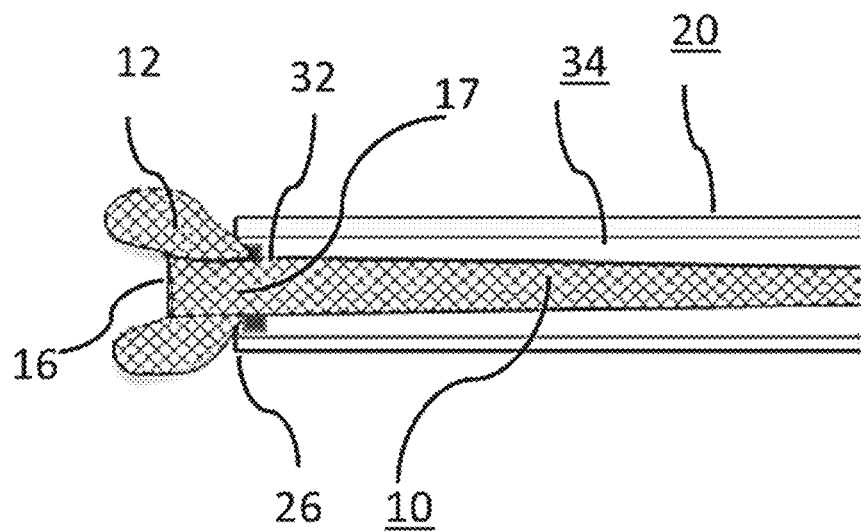
FIG. 5A is an enlarged schematic side view of the delivery system of FIG. 2 along section B-B of FIG. 4.
Figure 5B:
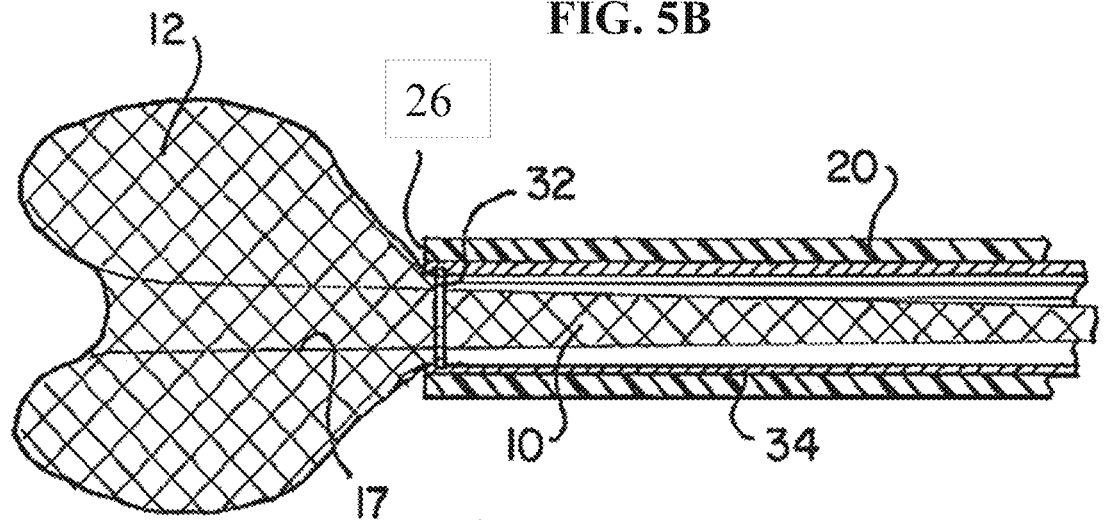
FIG. 5B is an enlarged schematic side view of the delivery system of FIG. 2 along section C-C of FIG. 4.

Such distal movement of mechanism 38 and initial formation of sack 12 of braid 10 is more clearly shown in FIG. 5A which is an enlarged view of section B-B of FIG. 4. As distal implant end 16 of braid 10 distally translates toward aneurysm A and away from end 26 of microcatheter 20, the distal implant end 16 of braid 10 can begin to invert and fold into itself thereby beginning to form an occlusive sack 12 for occluding an aneurysm. This is more clearly shown in FIG. 5B, which is an enlarged view of section C-C of FIG. 4. Mechanism 38 may be driven by a hypotube from its proximal end by an operator or the like. It is understood that braid 10 can also be attached to and/or foldable over an inner portion of mechanism 38, for example at attachment 36.

Figure 5C:
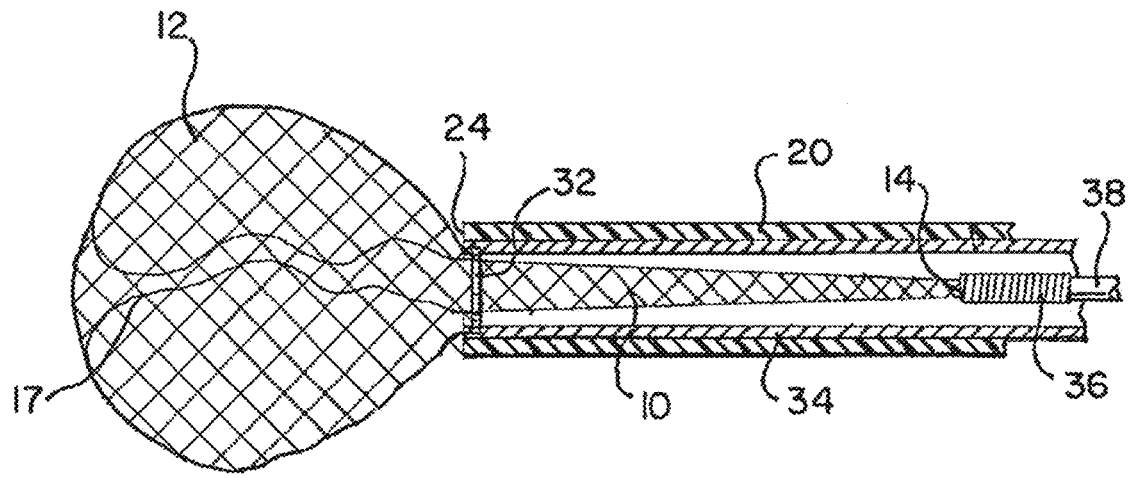
FIG. 5C is an enlarged schematic side view of the delivery system of FIG. 2 along section D-D of FIG. 4.

In step 420, mechanism 38 may continue to be distally translated while distal implant end 16 of braid 10 continues inverting as it approaches or contacts the dome of aneurysm A. Braid 10 can also begin inverting immediately as it exits catheter 20 (see, e.g., step 410 of FIG. 5A). It can be seen that sack 12 has now completely expanded into its predetermined, spherical shape designed to conform to the shape of aneurysm A. This is more clearly shown in FIG. 5C which is an enlarged view of section D-D, wherein sack 12 can be seen in the spherical shape. More specifically, in moving between steps 405 and 420 as shown between FIGS. 5A-5C, mechanism 38 distally translates braid 10 until braid folds about its distal implant end 16 to form the sack 12. Sack 12 may take on any shape necessary to occlude the respective aneurysm A.

Figure 5D:
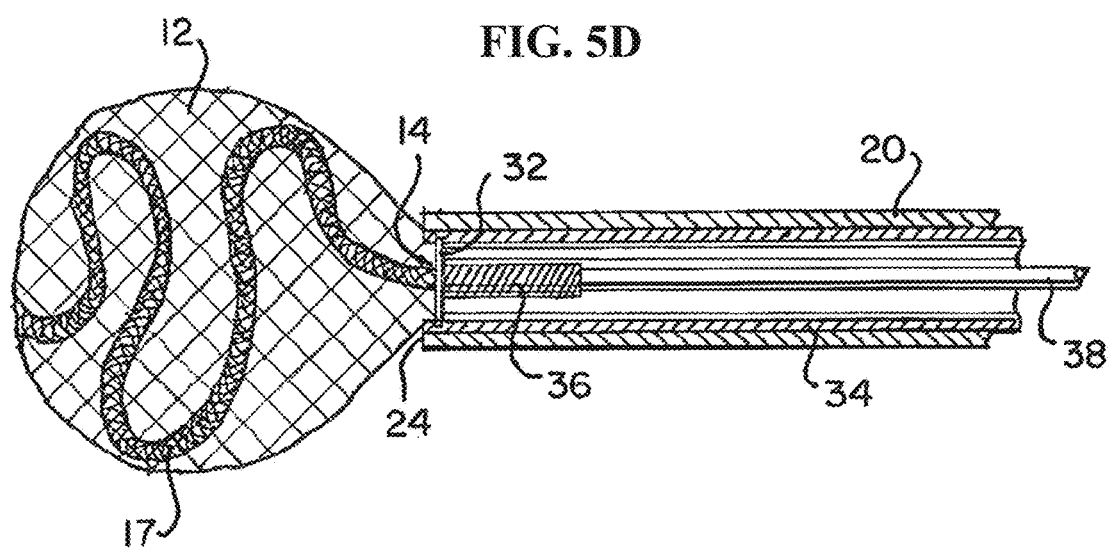
FIG. 5D is an enlarged schematic side view of the delivery system of FIG. 2 along section E-E of FIG. 4.

Between steps 420 to 425, mechanism 38 continues to distally slide until unexpanded, braid portion(s) 17 proximal of sack 12 folds and randomly fills sack 12, as shown more particularly in FIG. 5D, which is an enlarged view of section E-E. Sack 12 can be the depicted spherical shape and formed to impart a predetermined packing density and portion 17 which is formed with braid 10 has filled sack 12 to further reinforce sack 12. In other words, as the braid 10 reaches the dome of the aneurysm, the braid portion(s) 17 proximal to sack 12 coming from mechanism 38 can be forced to deflect and start filling the sack 12 as shown starting in step 415.

In step 430, with the sack 12 fully formed in a manner sufficient to occlude aneurysm A, braid 10 can be detached from attachment 36. However, if sack 12 is not precisely positioned or if needs to be reset within aneurysm A for safe occlusion without risk of rupture, braid 10, including sack 12, can be retracted back into delivery tube 34 by proximally moving mechanism 38. It is understood that when sack 12 is fully formed, it is capable of packing aneurysm A with a 15-25% packing density without the need for any embolic coils. However, braid 10 can be designed to achieve a packing density of 40%, 50%, or less than 15-25%, as needed or required. The change in packing density can be affected by changing the length or diameter of the braid 10. A longer or shorter braid 10 in the same aneurysm A can change the amount of braid deployed, which in turn can dictate the number of sacks 12 formed and the amount of unexpanded, braid portion 17 filling the sack 12. The same can hold true for the diameter of the braid 10, a larger diameter filling more of the aneurysm A in less length, but at a lower density. The operator can then choose between the differing parameters of a braid 10 for each particular aneurysm A.

In step 435, because sack 12 has been properly positioned and formed within aneurysm A, braid 10 has been detached from mechanism 38 and mechanism 38 can now be retracted therefrom. As shown, opposing grasper arms 42a, 42b can be formed with the microcatheter 20 or delivery tube 34 and withdrawn proximally so arms 42a, 42b can release sack 12 formed by expanding braid 10. It is understood that some or all of arms 42a, 42b can be radiopaque so that positioning and detachment can be monitored and/or driven under fluoroscopy.

Figure 6A:
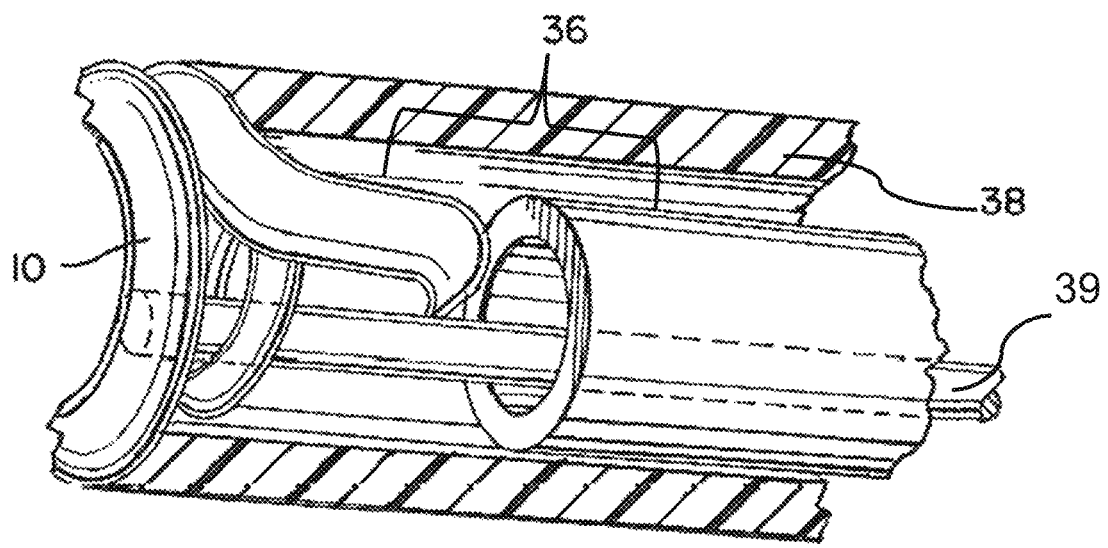
FIG. 6A is an enlarged perspective schematic view of section F-F across its center line showing an exemplary proximal implant end of the braid in communication with an exemplary pushing mechanism.

One example of attachment 36 is shown in FIG. 6A which is an enlarged perspective schematic view of section E-E of step 425 across center line in order to show braid 10 in communication with mechanism 38. It can be seen that mechanism 38 may include a pull wire 39 that hooks into or attaches to braid 10 and similarly can be released therefrom and that attachment will be secure so long as pull wire 39 is not pulled proximally. If pull wire 39 is pulled back braid 10 can be released. FIG. 6A is merely one way that mechanism 38 may attach to braid 10 across attachment 36 and any number of attachment means are contemplated as needed or required.

Figure 6B:
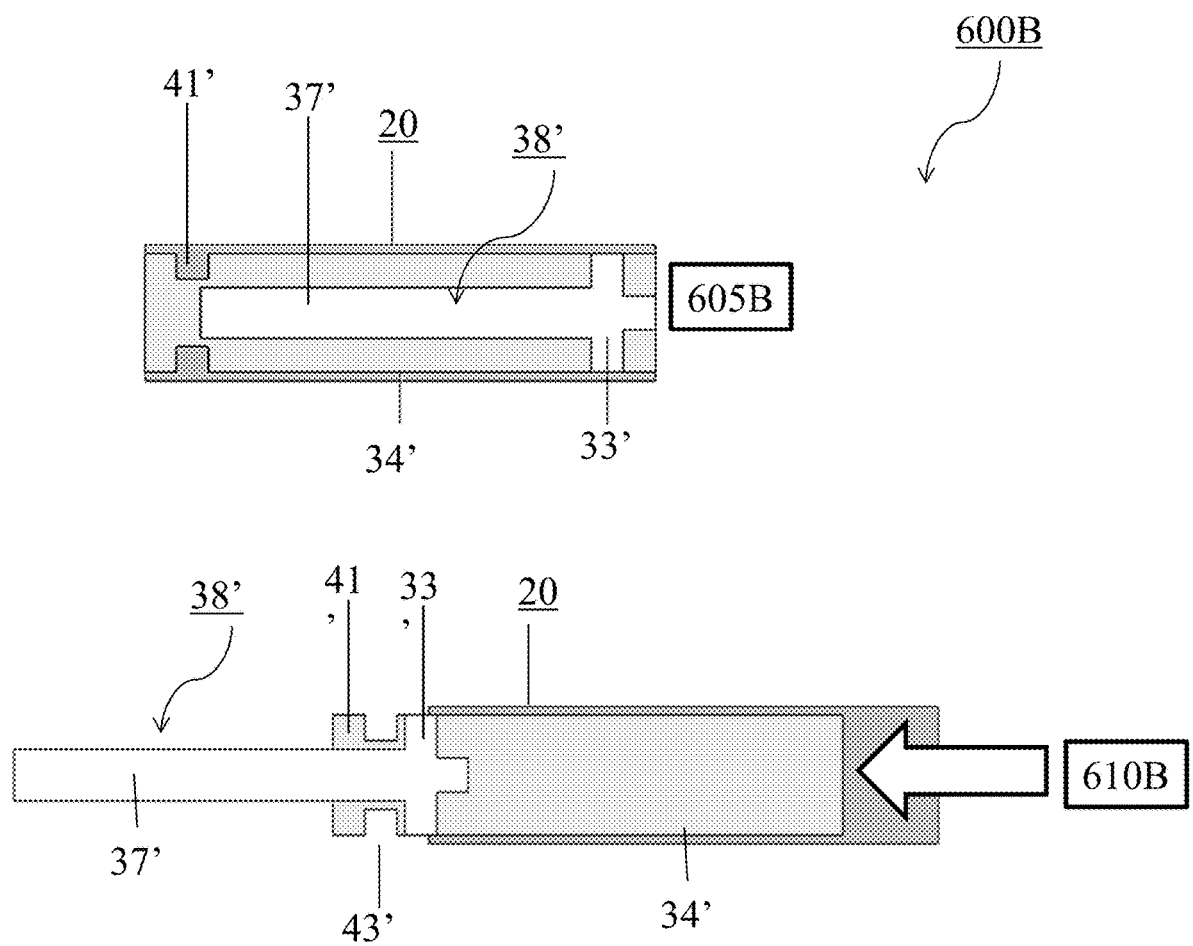
FIG. 6B is an enlarged schematic overview showing an exemplary attachment system as between a delivery tube, pushing mechanism and catheter in an embodiment of the delivery system.

Another example of how system 30 may release braid 10 is shown in FIG. 6B. In a first step 605B of method 600B, mechanism 38' is shown in a collapsed condition within delivery tube 34' and catheter 20. Mechanism 38' includes a substantially elongate portion 37' that generally runs along the inner cavity or lumen of tube 34' leaving a space between the elongate portion 37' and the tube 34'. Portion 37' may be axially aligned with tube 34'. A base portion 33' of mechanism 38' may also be included disposed on a proximal end of mechanism 38'. Portion 33' may at least be wider than portion 37' and can extend to the inner surface of tube 34'. During use, braid 10 can be axially positioned over the space between portion 37' and tube 34', advanced over portion 37', and secured to portion 33'. In step 610B, it can be seen that mechanism 38' has been distally translated so that portion 37' is now distal of tube 34' and catheter 20. Base 33' has similarly been distally translated until it contacts protrusions 41' of tube 34'. When base 33' contacts protrusion 41' in step 610B, protrusion 41' will be distal of tube 34' so that proximal implant end 14 of braid 10 is free to detach. Protrusion 41' may also include a gap or space 43' into which end 14 of braid 10 can be attached. When space 43' is distal of catheter 20 and tube 34', in those embodiments where end 14 was previously fastened at space 43', end 14 may now freely disengage and release.

Protrusions 41' may be members or extensions of tube 34' that inwardly protrude to reduce the inner diameter thereabout to be less than a diameter of base 33'. In this regard, only one protrusion 41' may be provided integrally formed with tube 34' or detachably connected and positioned therewith. However, method 600B is not so limited and more than one protrusion 41' can be provided as well as a cylindrical protrusion 41', or any other protrusion shaped and designed to reduce the inner diameter to prevent base 33' from moving passed.

Figure 6C:
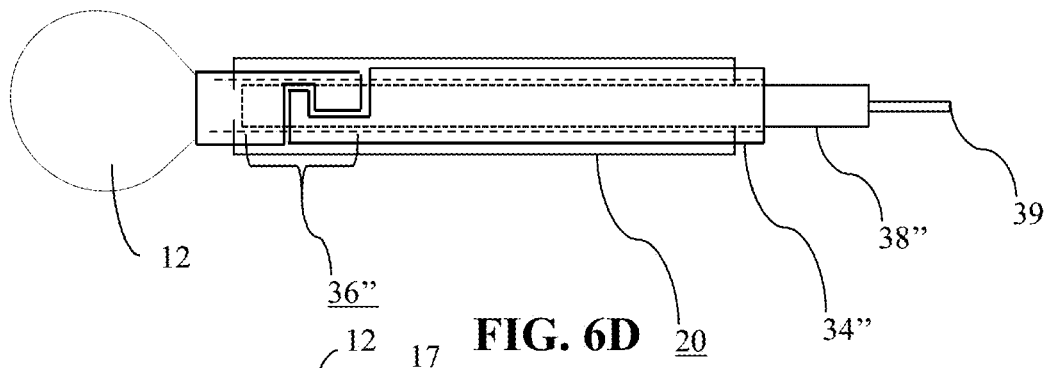
FIG. 6C is an enlarged schematic view showing an exemplary attachment system as between a delivery tube, pushing mechanism and catheter in an embodiment of the delivery system.
Figure 6D:
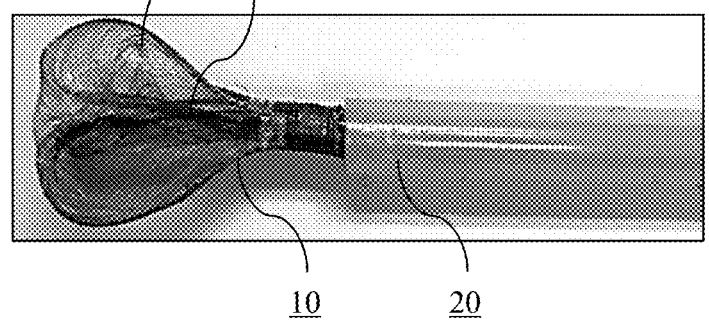
FIG. 6D is an enlarged schematic view showing an exemplary attachment system as between a delivery tube, pushing mechanism and catheter in an embodiment of the delivery system.
Figure 6E:
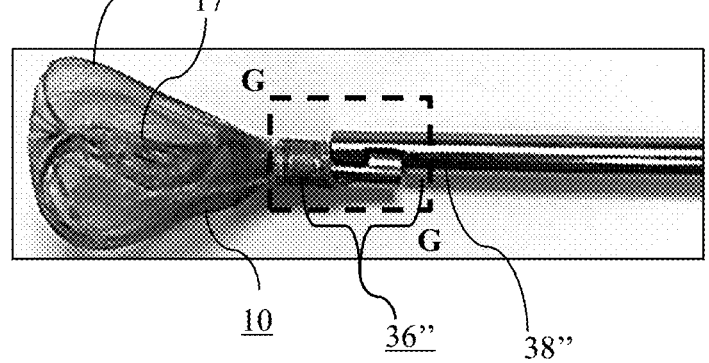
FIG. 6E is an enlarged schematic view showing an exemplary attachment system as between a delivery tube, pushing mechanism with the catheter removed in an embodiment of the delivery system.
Figure 6F:
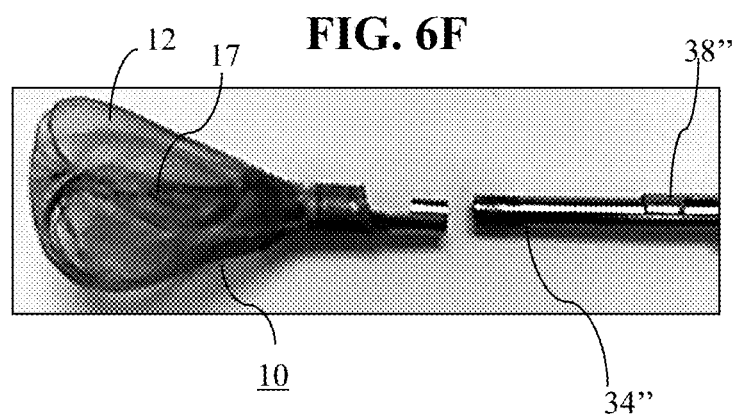
FIG. 6F is an enlarged schematic view showing an exemplary attachment system as between a delivery tube, pushing mechanism with the catheter removed in an embodiment of the delivery system.

Another example of how system 30 may release braid 10 is shown in FIG. 6C-FIG. 6F. In FIG. 6C, a schematic is shown of an exemplary prototype. FIG. 6D is a photograph of an exemplary prototype exemplifying the embodiment shown in FIG. 6C. Braid 10 is depicted in both FIGS. 6C and 6D in a deployed condition wherein sack 12 is formed distal of catheter 20 and tube 34". Mechanism 38" in this embodiment is mechanically attached to braid 10 via attachment 36", as more clearly shown in FIGS. 6E and 6F. Specifically, in FIG. 6E, catheter 20 has been removed to show braid 10 interconnected with mechanism 38" at attachment 36". In FIG. 6F, mechanism 38" has been detached from braid 10. In practice, mechanism 38" and catheter 20 can now be removed from the vasculature and from the patient altogether leaving occlusive sack 12 selectively positioned and formed to occlude aneurysm A.

Figure 7:
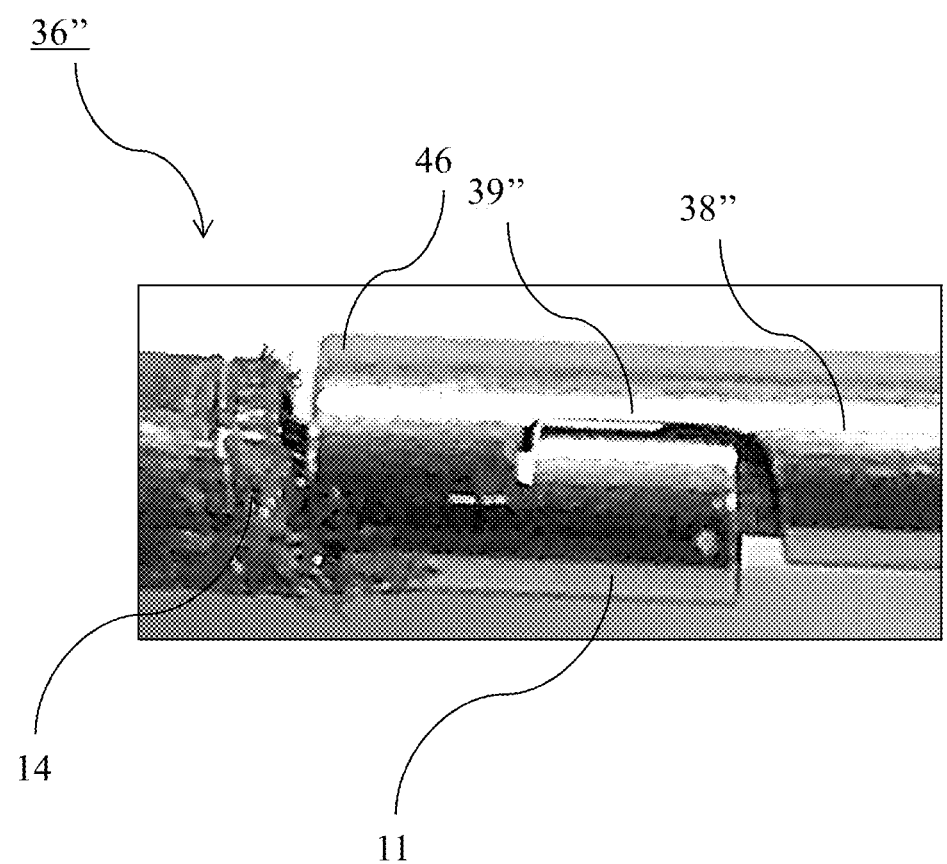
FIG. 7 is an enlarged schematic side view of the attachment system of FIG. 6E along section G-G.

Attachment 36" is more clearly shown in FIG. 7 which is an enlarged perspective schematic view of section G-G of FIG. 6E showing end 14 of braid 10 in communication with mechanism 38". It can be seen that mechanism 38" may include a releasable attachment interface formed by an interlinking member 39" about its distal end 46. Member 39" may be integrally formed with mechanism 38" and be constructed from a recess or channel portion operable to securely engage with attachment portion 11 of braid 10. Portion 11 may in turn be a separate portion fastened to, formed with, or otherwise disposed on end 14 of braid 10. Portion 11 may include a corresponding channel or recess operable to detachably, securely engage with member 39". In practice, member 39" may be securely engaged with portion 11 within delivery tube 34 prior to delivery to the vasculature. However, the mechanism 38" and braid 10 are not so limited and engagement can occur contemporaneous with delivery of system 30 being delivered to the vasculature. When the operator desires to deliver and release sack 12 with aneurysm A, braid 10 may be advanced distally from catheter 20 and/or delivery tube 34 by moving mechanism 38". Once member 39" is distal of tube 34, corresponding portion 11 of braid 10 can be released therefrom. Mechanism 38" can then be retracted and system 30 can be removed from the location of interest in the vasculature. It is understood that FIG. 7 is merely one way that a pushing mechanism of the herein disclosed system 30 may attach and detach to end 14 of braid 10 across attachment 36" and any number of attachment means are contemplated as needed or required.

Figure 8:
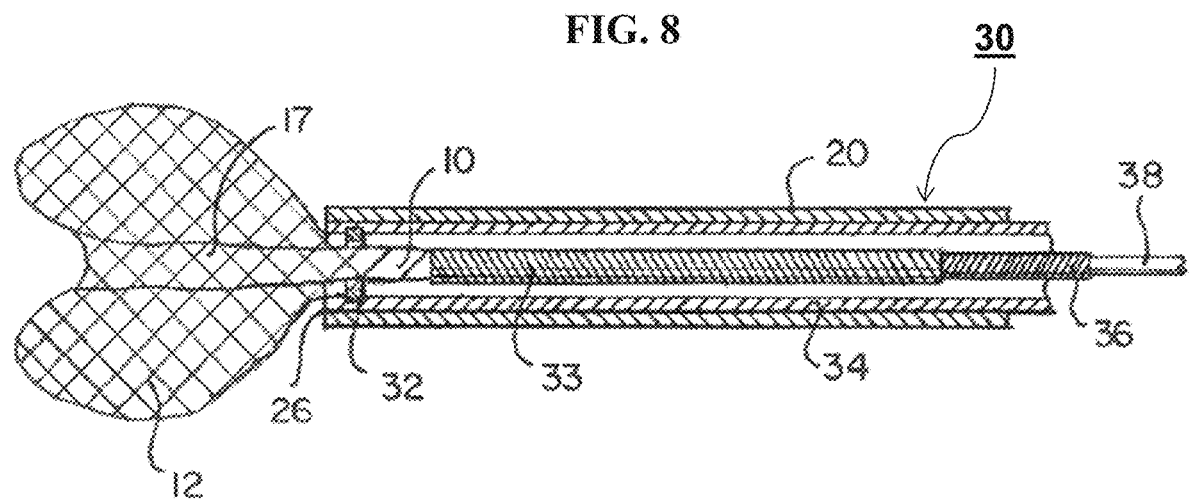
FIG. 8 is a schematic side view of an exemplary delivery system with an occlusion device being deployed with an embolic coil.

FIG. 8 is a schematic side view of another example delivery system 30 with device 1 in the process of being deployed and sack 12 in the process of being formed. In this embodiment, a coil 33 is also assembled with the delivery system 30 for later filling sack 12 to further facilitate packing of aneurysm A. It is understood that one or more additional coils can be inserted with proximal implant end 14 as needed or required. System 30 is not so limited, however, and braid 10 can include portions behind sack 12 that do not invert to form a sack. Instead, these aft portions are capable of being slid distally into formed sack 12 similar to adjusting a packing density delivered by sack 12 (see, e.g., FIGS. 12A-12I).

FIG. 9 is a flow diagram for a method 900 of delivering an occlusion device. In step 905, a self-expanding braid inverts as it distally translates from a delivery catheter into the aneurysm. In step 910, the braid forms an occlusive sack that conforms to the size and/or shape of the aneurysm. The braid may invert and/or radially expand in step 910 to form the occlusive sack. In step 915, the braid continues distally translating and when the braid reaches the top of the aneurysm, portions of the braid cease inverting (e.g., portions of the braid proximal the occlusive sack) and are in a non-inverted condition. In some embodiments, portions of the braid proximal the occlusive sack are in a non-inverted condition (e.g., unexpanded) as the braid is distally translated deeper into the aneurysm. In step 920, the portions of the braid in the non-inverted condition distally translate and fill the occlusive sack inside the aneurysm to a predetermined packing density. The density can be increased at least 25%, between 25-50%, or as much as 75% more than existing coil approaches.

FIG. 10 is a flow diagram for a method 1000 of delivering an occlusion device using the herein disclosed delivery system. Step 1005 includes selectively positioning a microcatheter in the vasculature. Step 1010 includes slidably positioning a delivery system of the occlusion device within the microcatheter, the delivery system comprising a delivery tube comprising a distal end and a proximal end and a pushing mechanism slidably disposed within the delivery tube, the pushing mechanism comprising a distal end and a proximal end. Step 1015 includes slidably positioning a self-expanding braid of the occlusion device within the delivery tube, the braid comprising a distal end and a proximal end. Step 1020 includes detachably attaching the proximal end of the braid to the distal end of the pushing mechanism. Step 1025 includes advancing the delivery system to the vasculature to the aneurysm. Step 1030 includes distally sliding the braid, by the pushing mechanism, in the delivery tube toward the aneurysm thereby causing the braid to invert and/or radially expand whiling moving from a collapsed condition within the delivery tube to a deployed condition within the aneurysm as the distal end of the braid is moved outside and away from the distal end of the delivery tube. Step 1035 includes releasing the occlusion device and withdrawing the delivery system and the catheter from the patient.

FIGS. 11A and 11B illustrate an example of the braid, or braided mesh 100. The mesh 100 can be self-expanding and which can be comprised of a tube of mesh. The self-expanding mesh 100 can include multiple wires 102, for example from 4 to 96 wires. The number of wires 102, and the diameter of the wires can be a factor in controlling the stiffness and pore size. y. For example, the distal end of the braid can more porous or more flexible than the proximal end, or vice versa. The combination of a braid with only one sack or multiple sacks (e.g., two or more sacks) can be taken into account when determining the number of wires. Fewer wires 102 can be used as a whole and still result in desired occlusion. The wires 102 can be made from multiple alloys such as a nickel-titanium alloy, cobalt chromium alloys, Platinum, Nitinol, Stainless Steel, Tantalum, or other alloys, or any other suitable biocompatible materials, or combination of these materials, including deposited thin films. Also, these materials can be absorbable or non-absorbable by the patient over time.

The apertures 104 in the mesh 100 create a substantially unitary frame work or mesh in the wall 106. Thus, the apertures 104 may be of any size, shape, or porosity, and may be uniformly or randomly spaced throughout the wall 106 of the mesh 100. The apertures 104 provide the tubular element with flexibility and also assist in the transformation of the mesh 100 from the collapsed state to the expanded state, and vice versa.

As discussed above, the mesh 100 inverts as it forms. This means that the inside 108 of the mesh 100 when the mesh is formed, becomes the "outside" on deployment or is in contact with the aneurysm A wall, as illustrated in FIG. 11B. For clarity, the mesh 100, is initially formed as a hollow cylindrical shape. This shape has an inside 108 and an outside. The inside 108 being akin to the hollow portion of a tube. Upon deployment, the mesh 100 is turned inside-out so the "inside" 108 on formation is now the "outside" of the sack 112 once deployed in the aneurysm A.

Note that the mesh 100 has a length L and that length L forms both the sack 112 and the unexpanded mesh 110 (or "tail") that forms within the sack 112. Controlling the length L can provide differing diameters of the sack 112, the number of internal sacks and/or the length of the tail 110 that fills the sack 112 and affects packing density.

In one example, the inversion of the mesh 100 can be formed when the proximal end 114 of the mesh 100 is pushed forward while the distal end 116 remains fixed. The proximal end 114 is pushed inside 108 forcing the proximal end 114 to exit the delivery tube first while end 116 remains fixed. Once the entire length L is deployed out of the delivery tube, the distal end 116 is detached and is thus the last end to be deployed. As above, the proximal end 114 engages the proximal implant end 14 and the distal end 116 engages the distal implant end 16. The mesh 100 can be formed akin to a tube sock.

Another example fixes the distal end 116 as above, and as the proximal end 114 is pushed, the mesh 110 just behind the distal end 116 is deployed, still causing the mesh 100 to deploy "inside out." Here, once the mesh 100 is fully deployed, both the proximal and distal ends 114, 116 are next to each other.

FIG. 11C illustrates the mesh 100 post-deployment with an embolic coil 330 at the proximal end 114 which can be opened. With end 114 being opened, the embolic coil 330 may be inserted therethrough to increase packing density of the corresponding occlusive sack or otherwise support the occlusive sack in certain aneurysm morphologies, such as aneurysms with wide necks. Coil 330 be made with any biocompatible materials commonly used in the art such as nickel-titanium alloy, cobalt chromium alloys, Platinum, Nitinol, Stainless Steel, Tantalum, or other alloys; or any other suitable biocompatible materials, or combination of these materials. The stiffness of the coil 330 can be adjusted by, for example, typical coil parameters of coil wire diameter, coil wound diameter, coil pitch, and coil material. In the instance of a coil, the diameter of the coil is selected in consideration of the size and shape of the aneurismal sac A, which can be a variety of shapes and sizes.

Figure 12A:
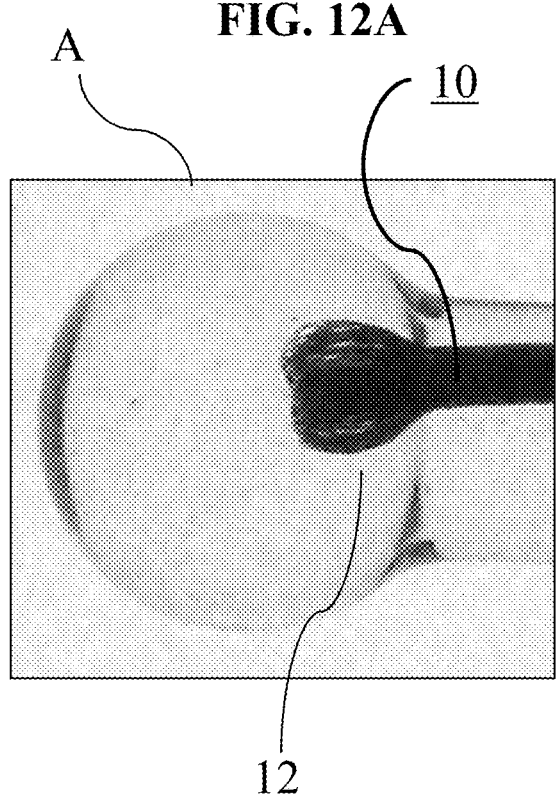
FIG. 12A is an enlarged view one step of an exemplary delivery system device being deployed into an aneurysm in accordance with this disclosure, wherein the system is shown moving from a collapsed condition to a deployed condition.
Figure 12B:
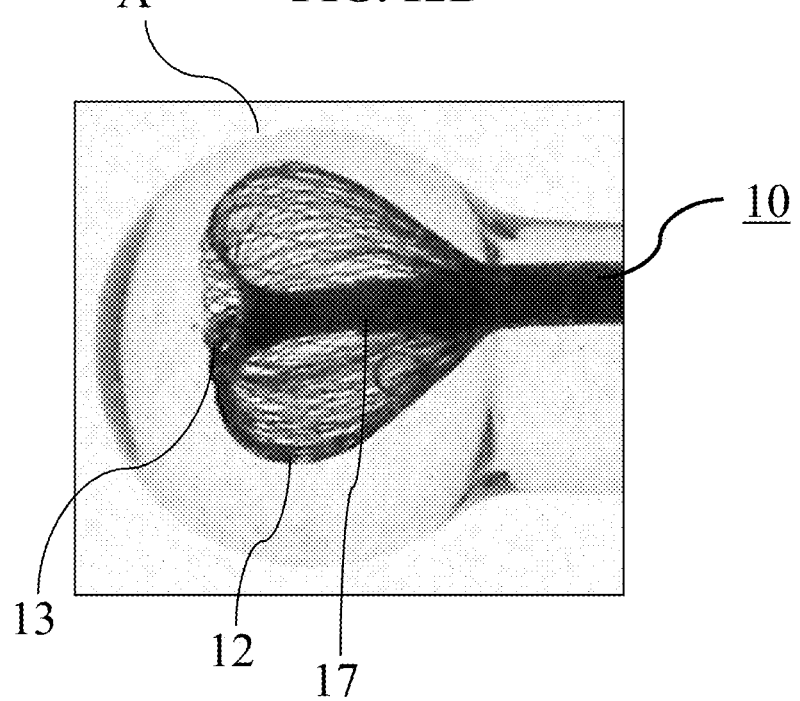
FIG. 12B is an enlarged view one step of an exemplary delivery system device being deployed into an aneurysm in accordance with this disclosure, wherein the system is shown moving from a collapsed condition to a deployed condition.

FIGS. 12A-12I depict example embodiments of braid 10 being delivered to an example aneurysm A. Specifically, in FIG. 12A, braid 10 can be seen being initially advance into aneurysm A and sack 12 beginning to take shape. In FIG. 12B, it can be seen that braid 10 continues to be distally advanced toward dome D of aneurysm A and folds into itself to form sack 12. However, braid 10 is not so limited and in certain embodiments as braid 10 exits catheter 20, braid 10 can begin inverting to form sack 12 without a break 13 and independent of its position relative to dome D. "The term "break" is used herein to include a region of the braid that facilitates inversion and/or avoid kinking of the braid during delivery. The break can include one or more local changes in physical properties with respect to other regions of the braid (e.g., increased flexibility, pre-weakened, etc.). Sack 12 is radially expanding toward the walls of aneurysm A while unexpanded portions 17 of braid 10 continue to be translated. It is understood that break 13 may be formed into the interstices of braid 10 so that inverted, folding occurs after braid 10 has distally translated a predetermined distance. Break 13 may include localized heat treatment to render braid 10 more ductile but kink preventative and induce a gradual folding curve. In this respect, the break 13, including localized heat treatment, can render braid 10 capable of expanding after inverting. Break 13 may also be simply be a weak point or buckling point pre-set for a particular sack 12 so that buckling is induced so as to avoid strain of aneurysm A. Alternatively, no break 13 may be included and instead braid 10 may invert and fold into itself upon contacting the dome D of aneurism A based on pre-selected pliability of braid 10.

In certain embodiments, sack 12 can be sized for only a specific sized aneurysm A. However, in other embodiments, sack 12 can be conformable or adjusted by the operator to sufficiently pack aneurysms across multiple sizes (e.g. across approximately 6 mm to approximately 10 mm) by continuing to advance portion 17 so that sack 12 is adjusted, as needed. For example, translating portion 17 distally from first to second positions can adjust from a first occlusion setting to a second setting. This is particularly advantageous in a clinical setting since it means that accurate measuring of aneurysm A is unnecessary and instead, sack 12 can be precisely and safely adjusted to fit aneurysm A in a manner that occludes without risk of rupture.

Figure 12C:
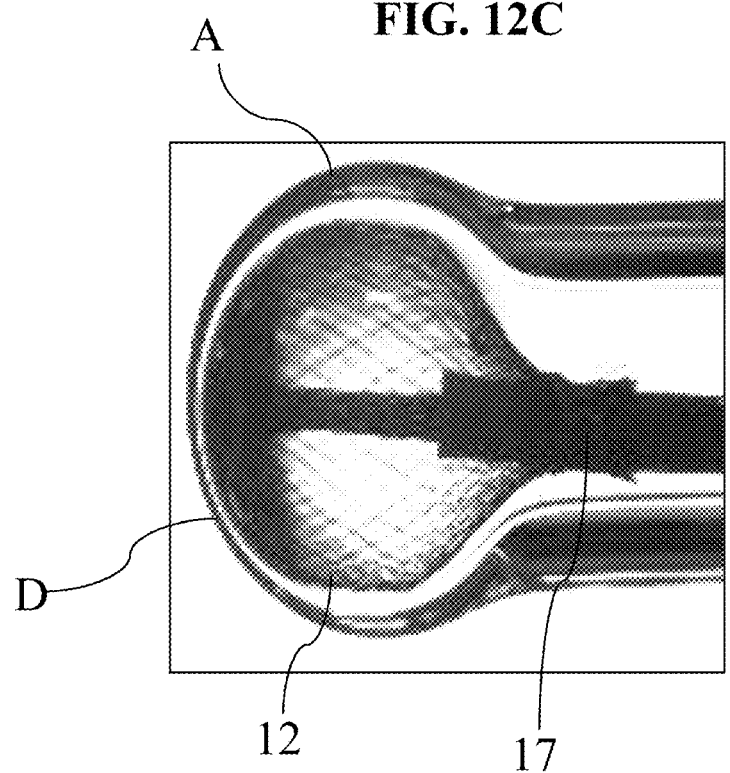
FIG. 12C is an enlarged view one step of an exemplary delivery system device being deployed into an aneurysm in accordance with this disclosure, wherein the system is shown moving from a collapsed condition to a deployed condition.
Figure 12D:
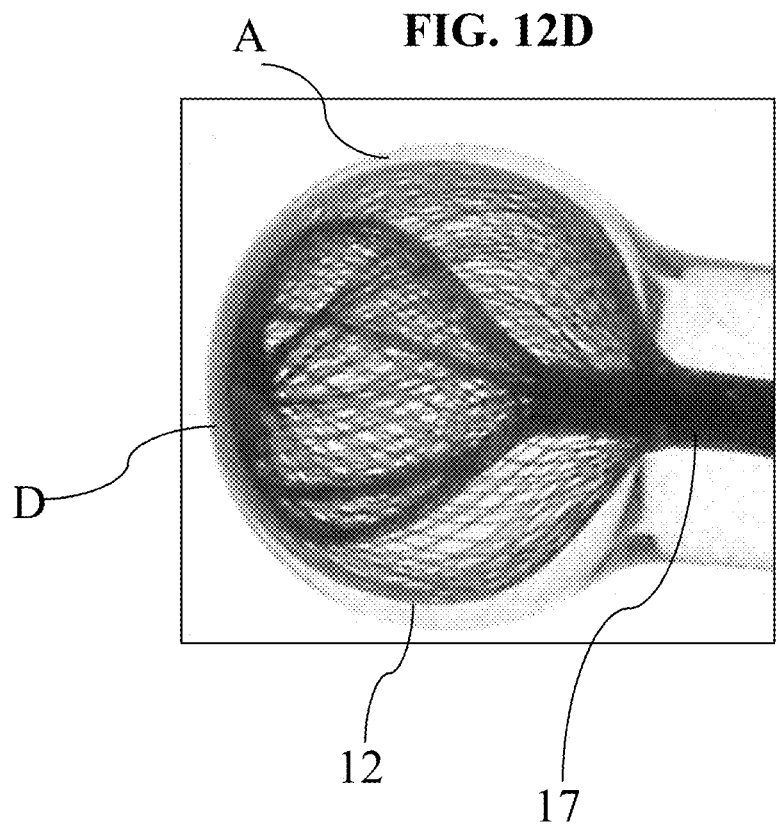
FIG. 12D is an enlarged view one step of an exemplary delivery system device being deployed into an aneurysm in accordance with this disclosure, wherein the system is shown moving from a collapsed condition to a deployed condition.
Figure 12E:
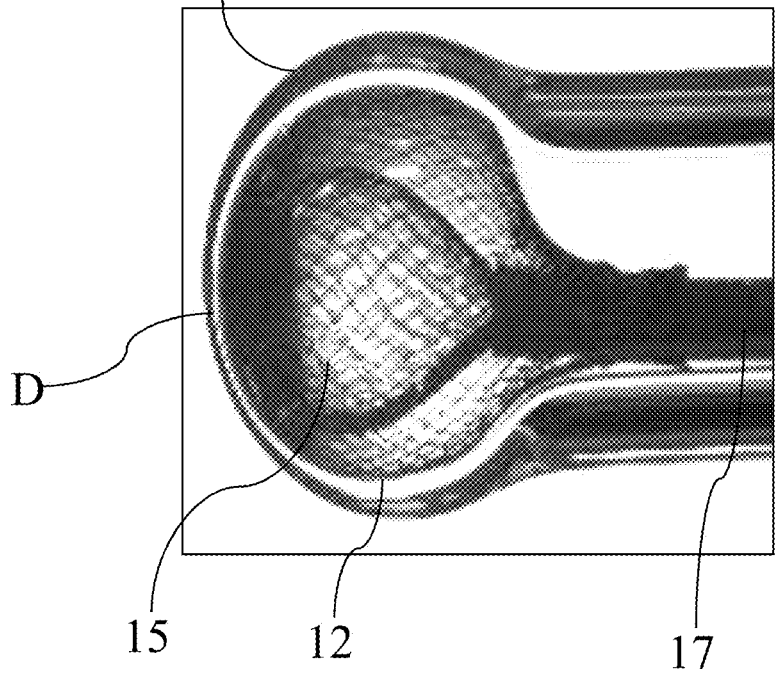
FIG. 12E is an enlarged view one step of an exemplary delivery system device being deployed into an aneurysm in accordance with this disclosure, wherein the system is shown moving from a collapsed condition to a deployed condition.
Figure 12F:
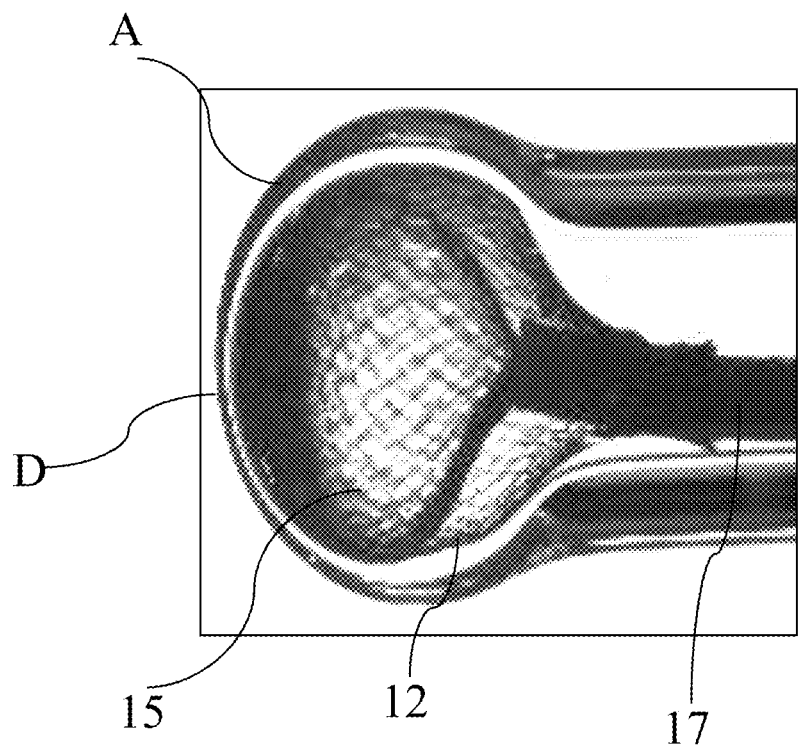
FIG. 12F is an enlarged view one step of an exemplary delivery system device being deployed into an aneurysm in accordance with this disclosure, wherein the system is shown moving from a collapsed condition to a deployed condition.
Figure 12G:
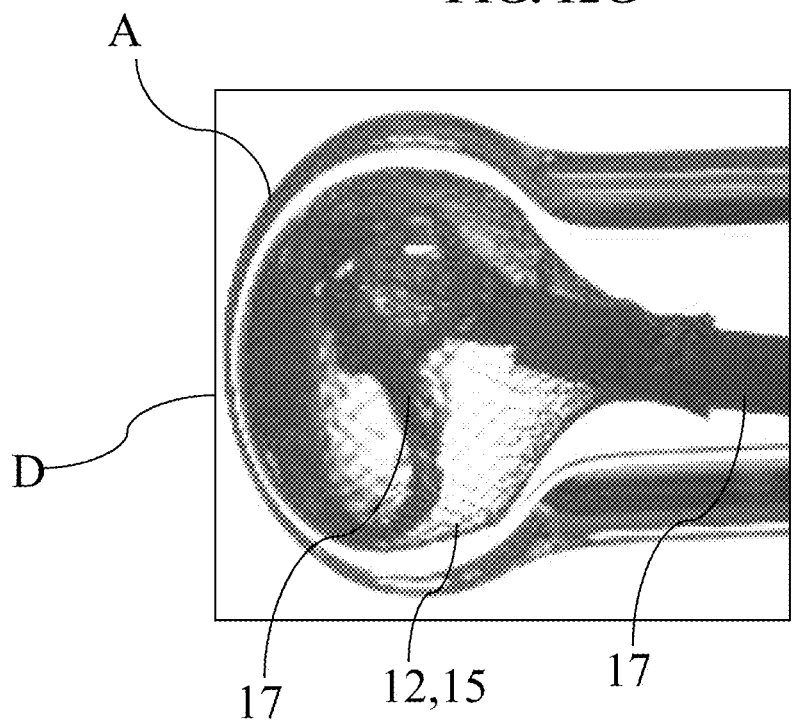
FIG. 12G is an enlarged view one step of an exemplary delivery system device being deployed into an aneurysm in accordance with this disclosure, wherein the system is shown moving from a collapsed condition to a deployed condition.
Figure 12H:
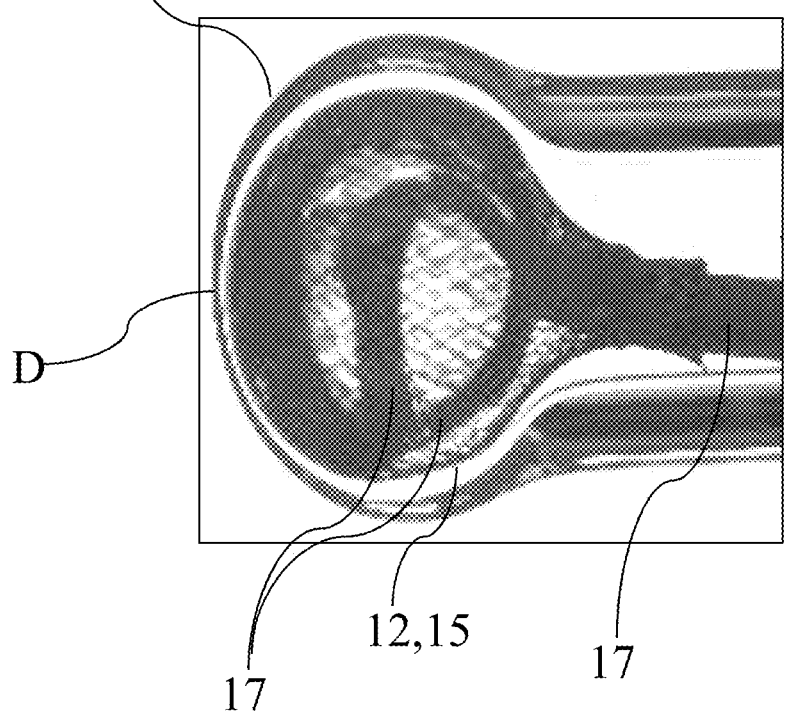
FIG. 12H is an enlarged view one step of an exemplary delivery system device being deployed into an aneurysm in accordance with this disclosure, wherein the system is shown moving from a collapsed condition to a deployed condition.
Figure 12I:
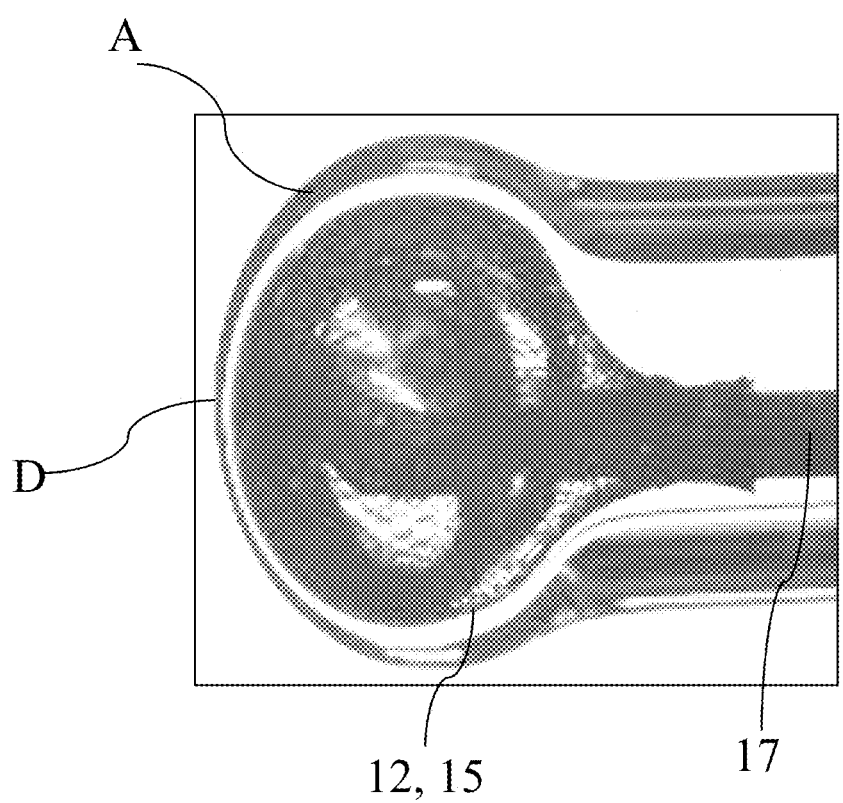
FIG. 12I is an enlarged view one step of an exemplary delivery system device being deployed into an aneurysm in accordance with this disclosure, wherein the system is shown moving from a collapsed condition to a deployed condition.

In FIG. 12C, sack 12 is nearly fully formed and in FIG. 12D, portions 17 have been distally translated so that sack 12 is fully formed with no additionally portions necessary to expand. In FIG. 12D specifically, it can be seen that formed sack 12 is now adjacent and supporting dome D. Braid 10 meanwhile may continue to be translated to form one or more additional sacks internal to sack 12 in order to overlay sack 12 to decrease porosity and/or further slow flow into the aneurysm. For example, in FIG. 12E, a second break may be included in braid 10 so that as portion 17 continues to be translated distally, a second sack 15 can begin to form and invert into itself. In FIG. 12F, portion 17 has distally translated more so that second sack 15 is now fully formed and overlaid internal to sack 12. In FIGS. 12G-12I, after formation of sacks 12, 15, portion 17 may continue to be distally translated while other portions of braid 10 no longer invert. In this respect, portion 17 can be considered a non-inverted portion of braid 10 proximal of sacks 12, 15. Portion 17 distally translates to fill sack 15 with portions 17, similar to a coil approach. However, unlike a coil approach, portions 17 can both fill sacks 12, 15 and then be retracted therefrom if an operator desires to re-position or re-set braid 10 with aneurysm A. The packing density of sack 12 can be adjusted by distally or proximally advancing portions 17 between one or more predetermined (e.g. a first setting of 15%, a second setting of 20%, a third setting of 25% etc). Rates of fluid occlusion can also be optimized by varying porosity throughout braid 10, including ends 14, 16, portion 17, and/or sacks 12, 15. The depicted embodiments here are merely example approaches of the herein disclosed braid 10. Other embodiments could include only one occlusive sack or more than two example occlusive sacks as depicted.

It is understood that variations of the braid 10 can include various materials such as stainless steel, bio absorbable materials, and polymers. Braid 10, including any specific portions such as any breaks and corresponding sacks, can be heat set to various configurations such as spherical, oblong, saddle shaped, etc. for the purpose of shaping the initial sack to better match the aneurysm morphology. In addition, the braid 10 can be heat shaped to include weak points to facility the braid buckling once it reaches the dome of the aneurysm.

It is also understood that any sack formed by the herein discussed braids 10 can be in a spherical shape as depicted or any other shape, as needed or required, such as ellipsoidal, heart-shaped, ovoid, cylindrical, hemispherical, or the like. Further, interstices of braid 10 that form the sack can vary, or be selectively designed, in size or shape along its length depending on how much braid 10 is caused to radially expand as pushing mechanism 38 is distally moved.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

ASPECTS OF THE INVENTION

1. A system for treating an aneurysm comprising:
a braid having a distal implant end opposite a proximal implant end, the braid having a lumen;
wherein the braid is configured such that distal translation of the proximal implant end toward the distal implant end causes the distal implant end to invert and fold into itself, thereby forming an occlusive sack for occluding an aneurysm.

2. The medical device of aspect 1, wherein the braid is a self-expanding braid.

3. The medical device of aspect 1 or aspect 2, wherein the outer surface of the braid is self-expanding.

4. The medical device of any preceding aspect, wherein the braid is configured to assume a predetermined occlusive sack shape.

5. The medical device of any preceding aspect, wherein the occlusive sack is configured to be substantially spherical in shape.

6. The medical device of any of aspects 1 to 5, wherein the occlusive sack is configured to conform in shape to an asymmetric aneurysm or an aneurysm with multiple sacs.

7. The medical device of any of aspects 1 to 5, wherein the occlusive sack is a collapsible cage-like vaso-occlusive structure.

8. The medical device of any preceding aspect, wherein an outer surface of the braid is comprised of a plurality of interstices.

9. The medical device of aspect 8, wherein dimensions of the interstices vary at the distal implant end versus the proximal implant end.

10. The medical device of any of aspects 1 to 7, wherein at least a portion of the braid defines a plurality of interstices with openings for occlusion of the aneurysm.

11. The medical device of any preceding aspect, wherein the braid is configured to be of a length sufficient that non-inverted portions of the braid not forming the occlusive sack fold into the occlusive sack, as distal translation continues, to increase packing density of the occlusive sack.

12. The medical device of any preceding aspect, wherein the proximal implant end is less pliable and/or has less material strength than the distal implant end.

13. The medical device of any preceding aspect, wherein the braid is further configured to form, upon continued distal translation, a second sack within the occlusive sack, each sack being formed from the braid inverting and folding into itself.

14. The medical device of any preceding aspect, wherein the braid further comprises a break disposed between the distal and proximal implant ends, the break configured to cause the occlusive sack to form when the distal implant end is distally translated toward the aneurysm.

15. The medical device of aspect 14 when dependent upon aspect 13, wherein the braid further comprises a second break disposed between the first break and the proximal implant end, the second break configured to cause the second sack to form upon continued distal translation.

16. The medical device of any preceding aspect, further comprising an embolic coil at the end of the proximal implant end.

17. The medical device of any preceding aspect, further comprising a delivery system; wherein the proximal implant end or embolic coil is operable to attach mechanically to the delivery system, the delivery system comprising a catheter and a pushing mechanism disposed in the catheter, the pushing mechanism operable to translate the braid.

18. A delivery system for an occlusive device for treating an aneurysm, comprising:
a delivery tube comprising a distal end and a proximal end, the delivery tube being slidably disposable within a microcatheter; and
a pushing mechanism slidably disposed with or within the delivery tube, the pushing mechanism comprising a distal end and a proximal end;
the medical device of any of aspects 1 to 16 slidably disposed within the delivery tube and mechanically attached to the pushing mechanism,
wherein the pushing mechanism is operable to distally translate the medical device to a deployed condition for occluding the aneurysm;
wherein the translation is in a distal direction thereby forming the occlusive sack for the aneurysm.

19. The system of aspect 18, wherein the distal implant end of the braid is detachably attached adjacent the distal end of the delivery tube such that the braid begins inverting to form the occlusive sack immediately as the braid exits the distal end of the delivery tube.

20. The system of any of aspects 18 and 19, further comprising:
an imaging device operatively connected to the occlusive device, wherein the imaging device is capable of imaging the sack with respect to the aneurysm; and
wherein an orientation and/or packing density of the occlusive sack is adjustable by the braid being distally or proximally moved.

21. The system of any of aspects 18 to 20, wherein the proximal implant end of the braid is detachably attached to the distal end of the pushing mechanism.

22. The system of any of aspects 18 to 21, wherein the proximal implant end of the braid is attached to and foldable over an inner portion of the pushing mechanism.

23. The system of any of aspects 18 to 22, wherein the distal end of the delivery tube comprises opposed gripping arms, one or both gripping arms being pivotable away from the other gripping arm to release the braid from the delivery tube.

24. The system of any of aspects 18 to 23, wherein the pushing mechanism further comprises an inner passage through which at least one embolic coil is insertable into the braid when the braid forms a sack within the aneurysm.

25. The system of any of aspects 18 to 24, wherein the distal end of the pushing mechanism comprises radiopaque material.

What is claimed is:

1. A method of delivering an occlusion device to an aneurysm, comprising:
positioning the occlusion device within a tubular delivery tube, the tubular delivery tube comprising a distal end releasably connected to a distal implant end of the occlusion device,
the occlusion device comprising a self-expanding braided tubular implant comprising the distal implant end and a proximal implant end, the braided tubular implant being invertible about the distal implant end;
distally sliding the braided tubular implant toward the aneurysm thereby
expanding the distal implant end of the braided tubular implant from a collapsed condition to a deployed condition; and
causing the distal implant end of the braid to invert and fold into itself and form an occlusive sack configured to occlude the aneurysm.

2. The method of claim 1, wherein the distal implant end of the braided tubular implant begins expanding immediately as the braided tubular implant exits a distal end of the delivery tube.

3. The method of claim 1, further comprising:
selectively positioning a microcatheter in the vasculature; and
positioning the occlusion device assembled with the delivery tube inside the microcatheter.

4. The method of claim 1, wherein the sack when formed comprises a predetermined packing density range.

5. A method of delivering an occlusion device to an aneurysm, comprising:
positioning an occlusion device within a delivery tube, the occlusion device comprising a self-expanding braid;
distally sliding the braid toward the aneurysm thereby expanding a distal implant end of the braid from a collapsed condition to a deployed condition;
inverting the distal implant end of the braid to form an occlusive sack configured to occlude the aneurysm; and continuing to distally slide the braid toward the aneurysm after formation of the first sack thereby changing a packing density of the occlusive sack with one or more unexpanded portions of the braid.

6. The method of claim 5, the braid further comprising:

a first break defined by a size of the sack for packing the aneurysm; and a second break on the braid after of the first break; the method further comprising:

distally sliding the braid toward the aneurysm after formation of the first sack; and inverting the braid at the second break to form a second sack within the first sack.

7. The method of claim 5, further comprising:

distally sliding the braid toward the aneurysm after formation of the first sack; and inverting the braid to form a second sack within the first sack.

8. The method of claim 5, further comprising:

continuing to distally slide the braid toward the aneurysm after formation of the first sack thereby packing the sack with one or more unexpanded portions of the braid.

9. The method of claim 5, further comprising:

determining a position of the sack relative to the aneurysm; and if the position fails to satisfy a fitting threshold with the aneurysm, then proximally sliding the braid thereby causing the sack to collapse back into the braid; and withdrawing the braid from the aneurysm.

10. A system for an occlusive device for treating an aneurysm, comprising:

a delivery tube comprising a distal end and a proximal end, the delivery tube being slidably disposable within a microcatheter; and a pushing mechanism slidably disposed with or within the delivery tube, the pushing mechanism comprising a distal end and a proximal end;

the occlusive device being slidably disposed within the delivery tube and mechanically attached to the pushing mechanism, the occlusive device comprising a braid having a distal implant end and a proximal implant end, wherein distally translating the braid, by the pushing mechanism, causes the distal implant end to invert and fold into itself thereby forming an occlusive sack for the aneurysm.

11. The system of claim 10, wherein the distal implant end of the braid begins inverting to form the occlusive sack immediately as the braid exits a distal end of the delivery tube.

12. The system of claim 10, wherein the proximal implant end of the braid is attached to and foldable over an inner portion of the pushing mechanism.

13. The method of claim 1, further comprising:

occluding the aneurysm with the occlusive sack.

14. The method of claim 1, the distal implant end being substantially atraumatic or rounded and configured to minimize kinking of the braided tubular implant during inversion.

\* \* \* \* \*